US012680066B2

(12) United States Patent
Hernández Vera et al.

(10) Patent No.: US 12,680,066 B2
(45) Date of Patent: Jul. 14, 2026

(54) CASSETTE ASSEMBLY

(71) Applicant: GRADIENTECH AB, Uppsala (SE)

(72) Inventors: Rodrigo Hernández Vera, Uppsala (SE); Tobias Kamf, Uppsala (SE); David Rönnholm, Märsta (SE); Dylann Duncan Ceriani, San Diego, CA (US)

(73) Assignee: GRADIENTECH AB, Uppsala (SE)

( * ) Notice: Subject to any disclaimer, the term of this patent is extended or adjusted under 35 U.S.C. 154(b) by 1288 days.

(21) Appl. No.: 17/442,180

(22) PCT Filed: Apr. 1, 2020

(86) PCT No.: PCT/SE2020/050342

§ 371 (c)(1),
(2) Date: Sep. 23, 2021

(87) PCT Pub. No.: WO2020/204799

PCT Pub. Date: Oct. 8, 2020

(65) Prior Publication Data

US 2022/0169966 A1     Jun. 2, 2022

Related U.S. Application Data

(60) Provisional application No. 62/828,725, filed on Apr. 3, 2019.

(51) Int. Cl.
C12M 1/00 (2006.01)
C12M 1/12 (2006.01)
(Continued)

(52) U.S. Cl.
CPC ............ C12M 23/34 (2013.01); C12M 23/38 (2013.01); C12M 23/42 (2013.01); C12M 25/02 (2013.01);
(Continued)

(58) Field of Classification Search
CPC ...... C12M 23/34; C12M 23/38; C12M 23/42; C12M 25/02; C12M 25/14; C12M 29/04;
(Continued)

(56) References Cited

U.S. PATENT DOCUMENTS 8,541,246 B2     9/2013 Bunce et al.
9,244,069 B2     1/2016 Bunce et al.
(Continued)

FOREIGN PATENT DOCUMENTS

CN         102149812 A      8/2011
CN         202033365 U     11/2011
(Continued)

OTHER PUBLICATIONS

Office Action from corresponding Chinese Application No. 2020800272902 dated Dec. 13, 2023.
(Continued)

*Primary Examiner* — William H. Beisner
*Assistant Examiner* — Danielle B Henkel
(74) *Attorney, Agent, or Firm* — Porter Wright Morris & Arthur LLP

(57) ABSTRACT

A cassette assembly (1) comprises a cover (100), two cassette halves (200A, 200B) and a slider (300) comprising multiple test chambers (302). The cassette halves (200A, 200B) comprise waste tanks (230) in fluid connection with reservoirs (240), prefilled in one of the cassette halves (200A, 200B) with test agents. The particular design of the cassette halves (200A, 200B) enable forming predefined 5 volumes of liquid to achieve predefined concentrations of the test agents in the reservoirs (240) in one of the cassette halves (200A, 200B) and liquid in the reservoirs (240) in the other of the cassette halves (200A, 200B). Gradients of the test agents can then be established over the multiple test chambers (302).

25 Claims, 24 Drawing Sheets

(51) Int. Cl.
    *C12M 1/34*     (2006.01)
    *C12M 3/00*     (2006.01)
    *G01N 33/50*     (2006.01)

(52) U.S. Cl.
    CPC ............ *C12M 25/14* (2013.01); *C12M 29/04* (2013.01); *C12M 41/40* (2013.01); *G01N 33/5008* (2013.01)

(58) Field of Classification Search
    CPC ... C12M 41/40; C12M 41/46; G01N 33/5008; B01L 2200/0605; B01L 2200/0621; B01L 2300/0864; B01L 2400/0487; B01L 2400/065; B01L 3/5025
    See application file for complete search history.

(56) References Cited

U.S. PATENT DOCUMENTS

| | | | |
|---|---|---|---|
| 9,415,392 B2 | 8/2016 | Ismagilov et al. | |
| 9,857,367 B2 | 1/2018 | Bunce et al. | |
| 10,487,349 B2 | 11/2019 | Kreuger et al. | |
| 10,543,485 B2 | 1/2020 | Ismagilov et al. | |
| 10,969,386 B2 | 4/2021 | Bunce et al. | |
| 11,427,851 B2 | 8/2022 | Kreuger et al. | |
| 2003/0175165 A1 | 9/2003 | Liu | |
| 2010/0035292 A1 | 2/2010 | Levhenko et al. | |
| 2011/0027914 A1 | 2/2011 | Bunce et al. | |
| 2011/0090779 A1 | 4/2011 | Yu et al. | |
| 2011/0207621 A1 | 8/2011 | Montagu et al. | |
| 2012/0028342 A1* | 2/2012 | Ismagilov | B01F 33/304 |
| | | | 422/503 |
| 2013/0040834 A1 | 2/2013 | Bunce et al. | |
| 2013/0115607 A1* | 5/2013 | Nielsen | C12Q 1/68 |
| | | | 435/6.12 |
| 2014/0171344 A1 | 6/2014 | Bunce et al. | |
| 2014/0278136 A1 | 9/2014 | Shamsheyeva et al. | |
| 2015/0247112 A1* | 9/2015 | Orr | C12M 29/10 |
| | | | 435/395 |
| 2015/0253251 A1* | 9/2015 | McKee | G01N 33/54366 |
| | | | 422/69 |
| 2016/0186231 A1 | 6/2016 | Kreuger et al. | |
| 2016/0256870 A1 | 9/2016 | Ismagilov et al. | |
| 2016/0288121 A1 | 10/2016 | Ismagilov et al. | |
| 2017/0023599 A1 | 1/2017 | Richards et al. | |
| 2017/0274378 A1 | 9/2017 | Turner et al. | |
| 2018/0120311 A1 | 5/2018 | Bunce et al. | |
| 2020/0048680 A1 | 2/2020 | Kreuger et al. | |

FOREIGN PATENT DOCUMENTS

| | | | |
|---|---|---|---|
| CN | 107570245 A | 1/2018 | |
| JP | 2012-521219 A | 9/2012 | |
| JP | 2016-523105 A | 8/2016 | |
| WO | 02/064253 A2 | 8/2002 | |
| WO | 2007/044888 A2 | 4/2007 | |
| WO | 2010/111265 A1 | 9/2010 | |
| WO | 2015/005863 A1 | 1/2015 | |
| WO | 2016/037051 A1 | 3/2016 | |
| WO | 2017/165852 A1 | 9/2017 | |

OTHER PUBLICATIONS

Search Report from corresponding European Application No. 20783330.2 dated Nov. 25, 2022.
Office Action from corresponding Japanese Application No. 2021-558797 dated Feb. 27, 2024 with English Translation.
Campbell, Jennifer et al., Microfluidic Advances in Phenotypic Antibiotic Susceptibility Testing, Biomed Microdevices, vol. 18, No. 6, pp. 1-17 (Dec. 2016).
Malmberg, Christer et al., A Novel Microfluidic Assay for Rapid Phenotypic Antibiotic Susceptibility Testing of Bacteria Detected in Clinical Blood Cultures, PLOS ONE, 11(12):e0167356, pp. 1-15 (Dec. 14, 2016).

* cited by examiner

PRESSURE
INTERFACE

112

100

PRESSURE
INTERFACE

113

1

400

CASSETTE ASSEMBLY

TECHNICAL FIELD

The embodiments generally relate to cassette assemblies for fluidic systems, and in particular to such cassette assemblies that can be used to determine a response of microorganisms to test substances or agents.

BACKGROUND

Antibiotic-resistant bacteria represent a growing global problem, as these bacteria cannot be killed or made to stop dividing by antibiotics. The generation time of bacteria can in many cases be very fast (around 20 minutes), and due to the short generation time and relative genetic instability of bacteria, the bacteria may quickly acquire resistance towards antibiotics. There is an increasing prevalence of antibiotic-resistant bacterial infections in the human population, and some of these bacteria have even become multi-resistant, sometimes meaning that there are no efficient antibiotics available to halt their growth. These multi-resistant bacteria are a serious public health problem as patients infected with such bacteria may die since their bacterial infections cannot be treated.

The traditional approaches for the identification and study of microorganisms, including but not limited to bacteria, fungi, parasites and viruses, and their resistance to test agents, such as antibiotics, which kill or inhibit the growth of the microorganism, have mainly, in the example of bacteria, been limited to broth micro dilution where varying concentrations of the antibiotics and the bacteria to be tested are added to different wells of a micro titer plate. After the allotted time, typically 16 to 20 hours, of incubation the wells are checked for bacterial growth by measuring the optical turbidity in the different wells.

The Kirby-Bauer test, which is basically an agar diffusion method, is also commonly used. Here wafers, or discs, that contain bactericidal or bacteriostatic antibiotics of defined concentrations are placed on agar plates where bacteria have been spread. The agar plates are left to incubate and if an antibiotic stops the bacteria from growing or kills the bacteria, a zone of inhibition will become visible after incubation.

Another prior art approach is the so-called E-test. The E-test uses a rectangular strip impregnated with different concentrations of a test agents to be evaluated for its killing or growth inhibiting effect. In a typical approach, bacteria are spread and grown in a 2D culture on an agar plate, where after the E-test strip is placed on top of the agar plate. The E-test strip releases the test agent by diffusion and the growth inhibitory effects of the released test agent are typically inspected after 24 hours of incubation.

The Kirby-Bauer test and the E-test as two-dimensional (2D) culture methods for antibiotic susceptibility testing (AST) and evaluation of the effects of antibiotics or other test agents on microorganisms have several limitations. For instance, these setups normally require that the microorganisms, e.g., bacteria, are cultured over night to allow for a clear result readout showing if a particular bacteria strain is resistant or not to a given antibiotic. A further limitation is that readouts of the inhibitory concentration of the test substance is only possible in distinct digital steps and in the selected concentrations used in the E-test strip. The shortcomings for the broth microdilution approach for traditional AST are basically the same.

In order to reduce the AST time, microfluidic channel systems for rapid AST (RAST) have been developed. Such RAST approaches include droplet-based microfluidic channel systems, in which bacteria are captured in a droplet that includes an antibiotic. A limitation with the droplet-based system is that only a single antibiotic concentration can be tested. Other RAST approaches include using polydimethylsiloxane (PDMS) microchannels, dielectrophoretic capturing of bacteria in microfluidic electrode structures, pre-loaded PDMS layers with antibiotics, covalently binding bacteria to microfluidic channels and subjecting them to mechanical shear stress, using asynchronous magnetic bead rotation (AMBR) biosensors or tracking single cell growth in a microfluidic agarose channel system. A major limitation of these various RAST approaches is that they can only test a single antibiotic concentration or a set of a few selected antibiotic concentrations.

It has further been proposed to use a microfluidic system for analysis of antibiotic susceptibility of bacterial biofilms. Such a microfluidic system, however, requires 24 hours of incubation and the bacteria to be tested must contain a plasmid able to express green fluorescent protein (GFP).

Hence, there is still a need for systems for response testing of microorganism that do not have the disadvantages of the prior art. There is a particular need for a cassette assembly that can be used in such systems.

SUMMARY

It is a general objective to provide a cassette assembly that can be used in systems for response testing of microorganisms.

This and other objectives are met by embodiments as disclosed herein.

The present invention is defined in the independent claim. Further embodiments of the invention are defined in the dependent claims.

An aspect of the invention relates to a cassette assembly comprising a cover, a first cassette half and a second cassette half and a slider. The cover is configured to be positioned onto the first and second cassette halves and keep the first and second cassette halves together with the slider sandwiched between the first and second cassette halves. The slider comprises N≥2 test chambers in the form of through holes through the slider. Each of the first and second cassette halves comprises N waste tanks connected in series and separated by respective walls and an excessive liquid tank in fluid connection with the waste tanks by a vertical outlet channel and by an air valve. An inlet port of the first cassette half is configured to receive a liquid caused to sequentially fill each waste tank and a head space defined above the waste tanks. Opening of the air valve causes drainage of liquid in the head spaces into the excessive liquid tanks through the vertical outlet channels and a separation of equal volumes of liquid in the waste tanks.

In an embodiment, the slider comprises a first through hole in connection with a first end of the slider and a second through hole in connection with a second end of the slider. In this embodiment, the first and second cassette halves each comprises a circumferential channel having a first opening configured to be aligned with the first through hole and a second opening configured to be aligned with the second through hole. Each of the first and second cassette halves also comprises a serpentine channel interconnecting the circumferential channel and the waste tanks. In this embodiment, the inlet port of the first cassette half is in fluid connection with the circumferential channel. The serpentine channels present a higher flow resistance to the liquid as compared to the circumferential channel to enable filling of the circumferential channels prior to entering of the liquid into the waste tanks through the serpentine channels.

The cassette assembly enables an accurate metering of predefined volumes of liquid in reservoir tanks to achieve accurate concentrations of test agents and controlled establishment of concentration gradients over 3D culture matrices in the test chambers. As a consequence, microorganisms present in a biological sample can be exposed to well-defined concentration gradients for the purpose of determining the response of the microorganisms to the test agents, including determination of minimum inhibitory concentration (MIC) values.

BRIEF DESCRIPTION OF THE DRAWINGS

The embodiments, together with further objects and advantages thereof, may best be understood by making reference to the following description taken together with the accompanying drawings, in which.

4

Figure 17:
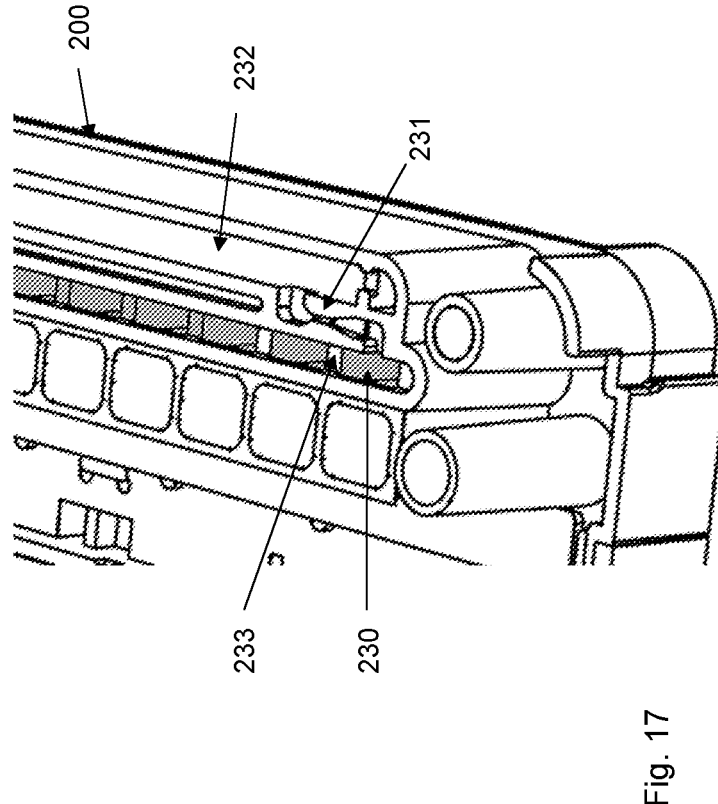
Figure 18:
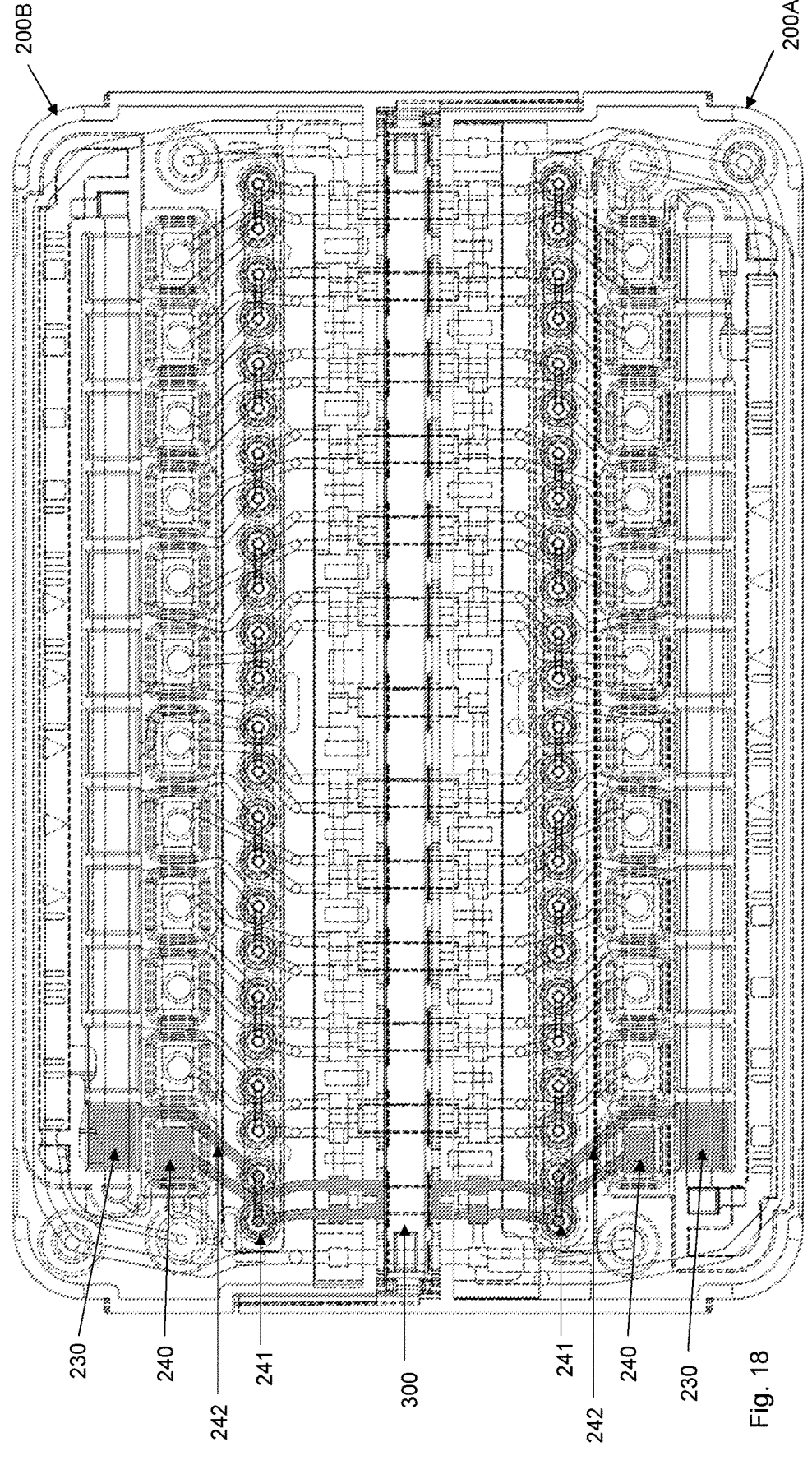
Figure 19:
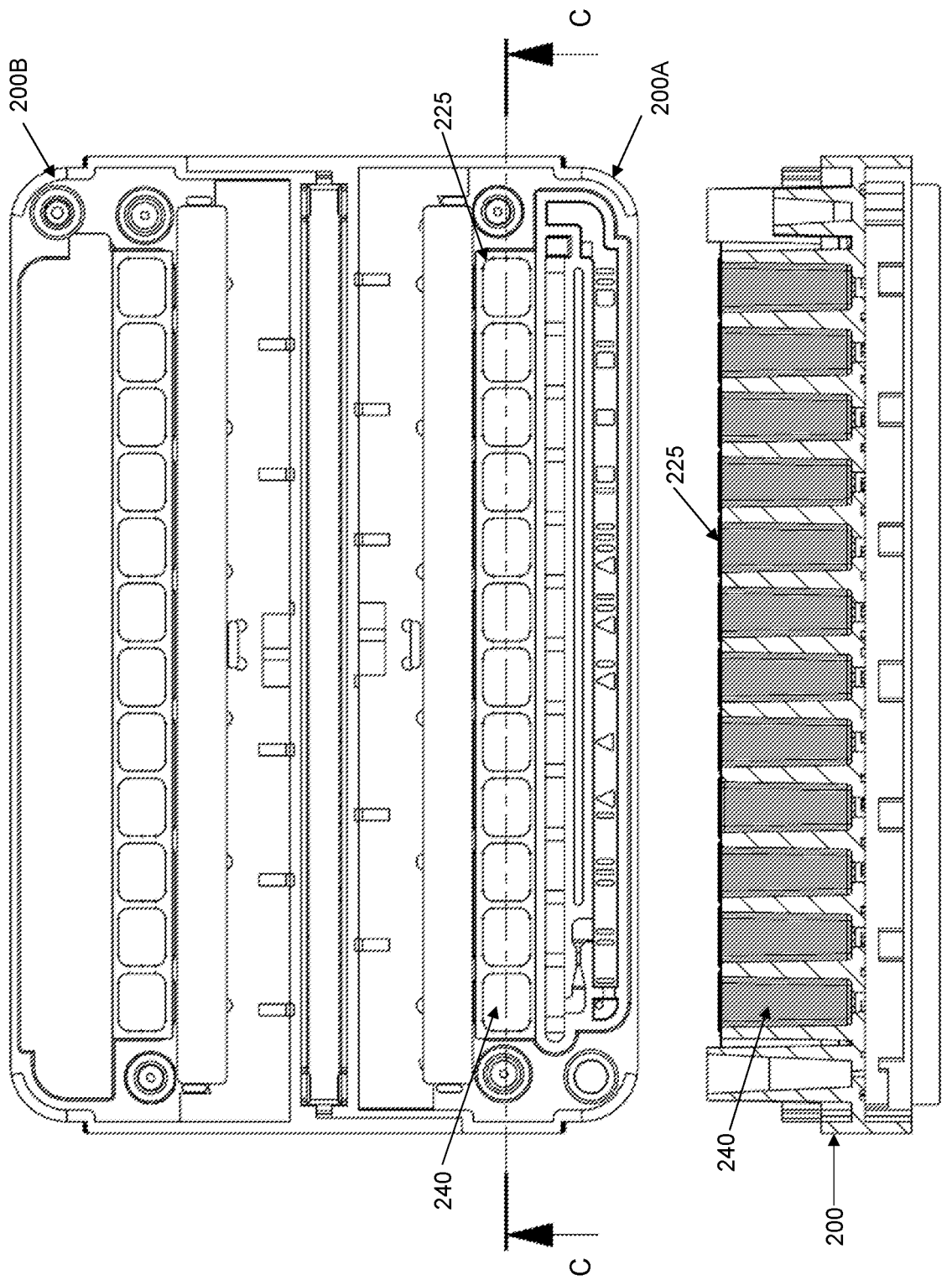
Figure 20:
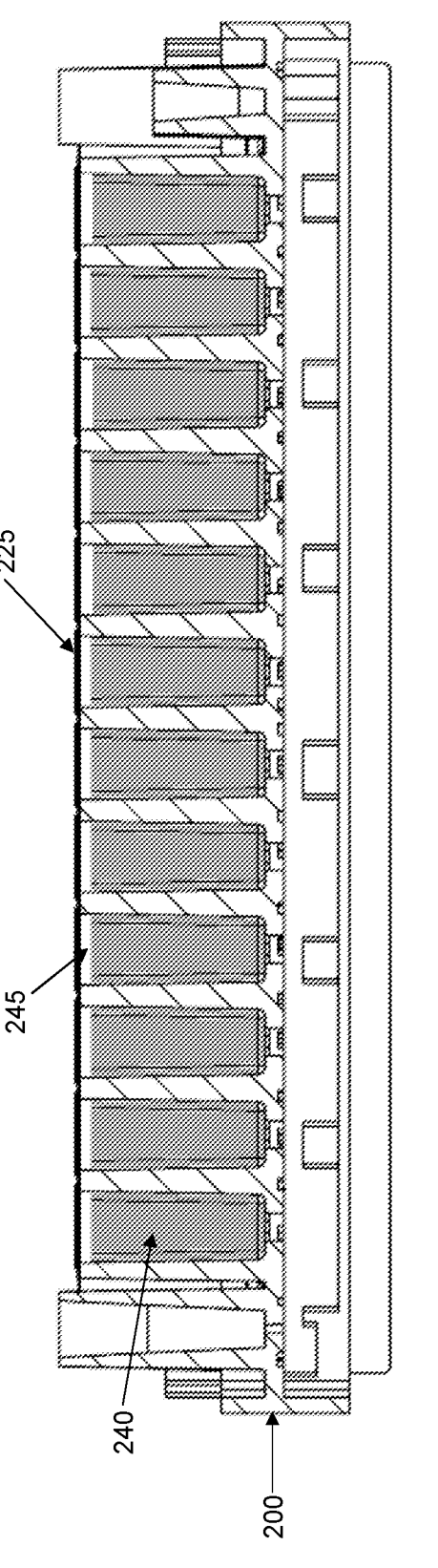
Figures 21, 22:
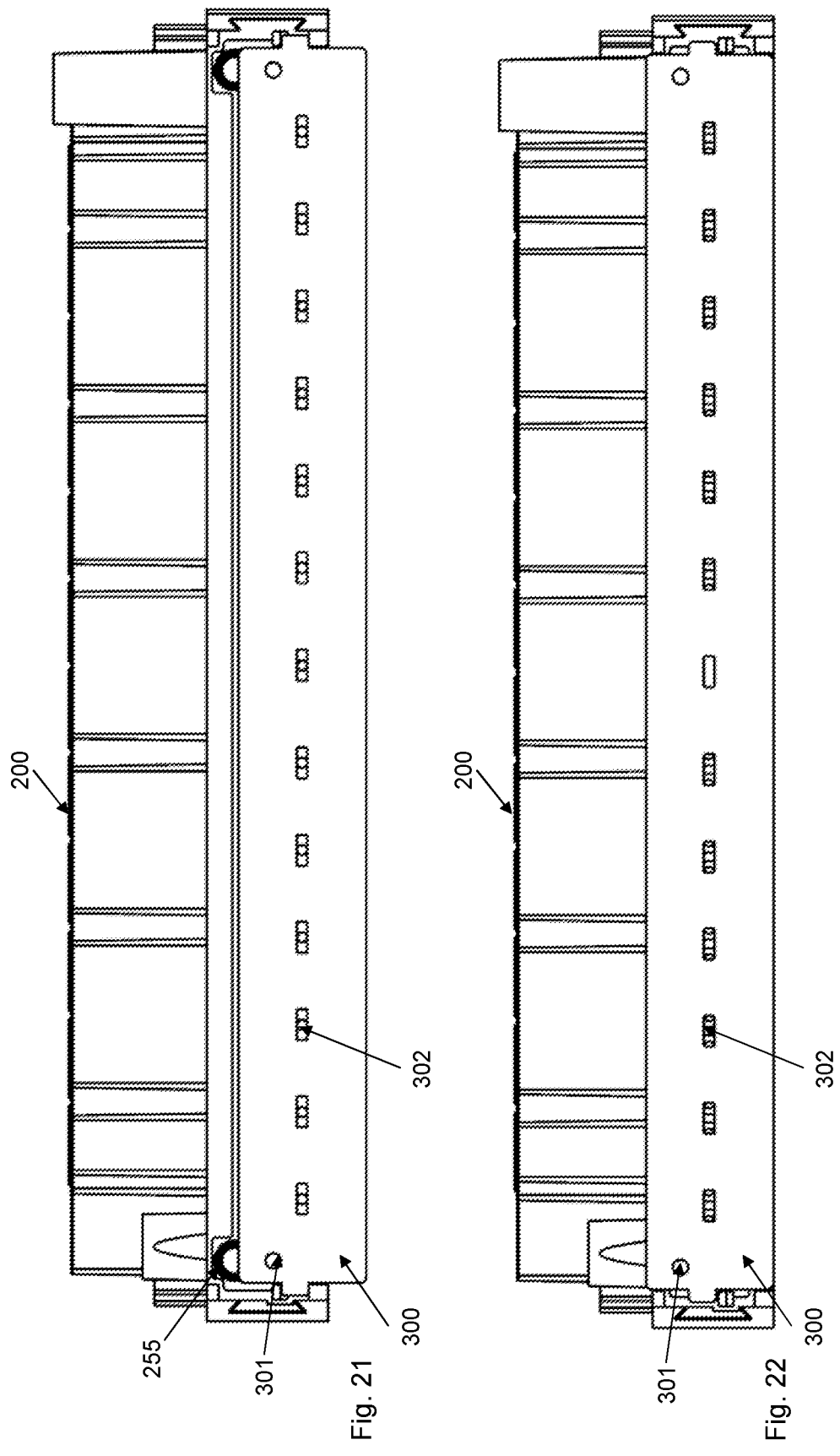
Figure 23:
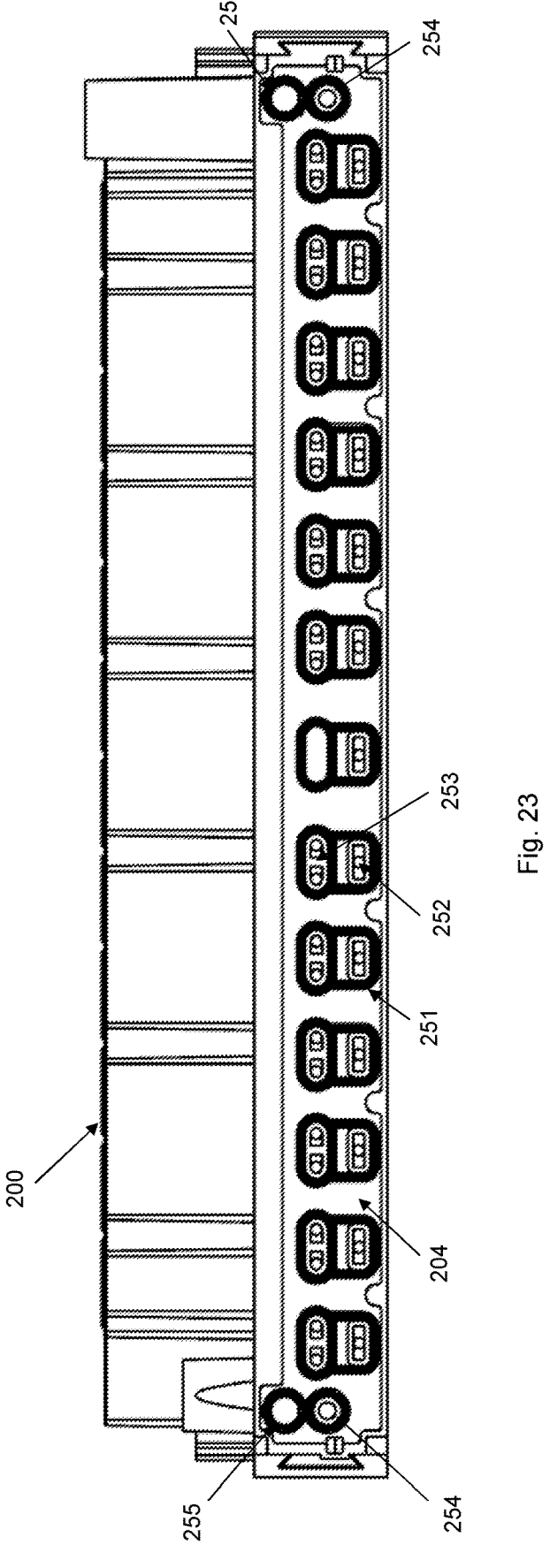
Figure 24:
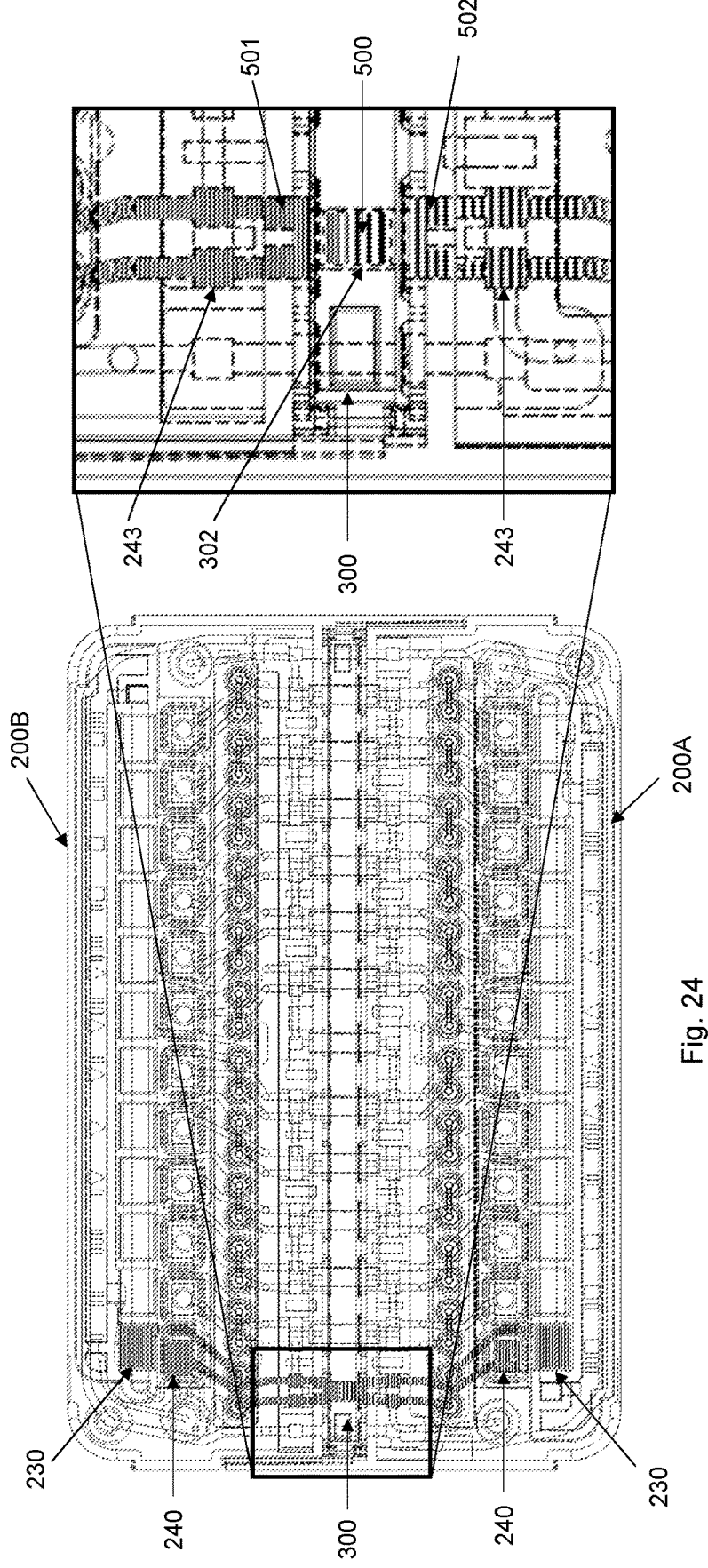
Figure 25:
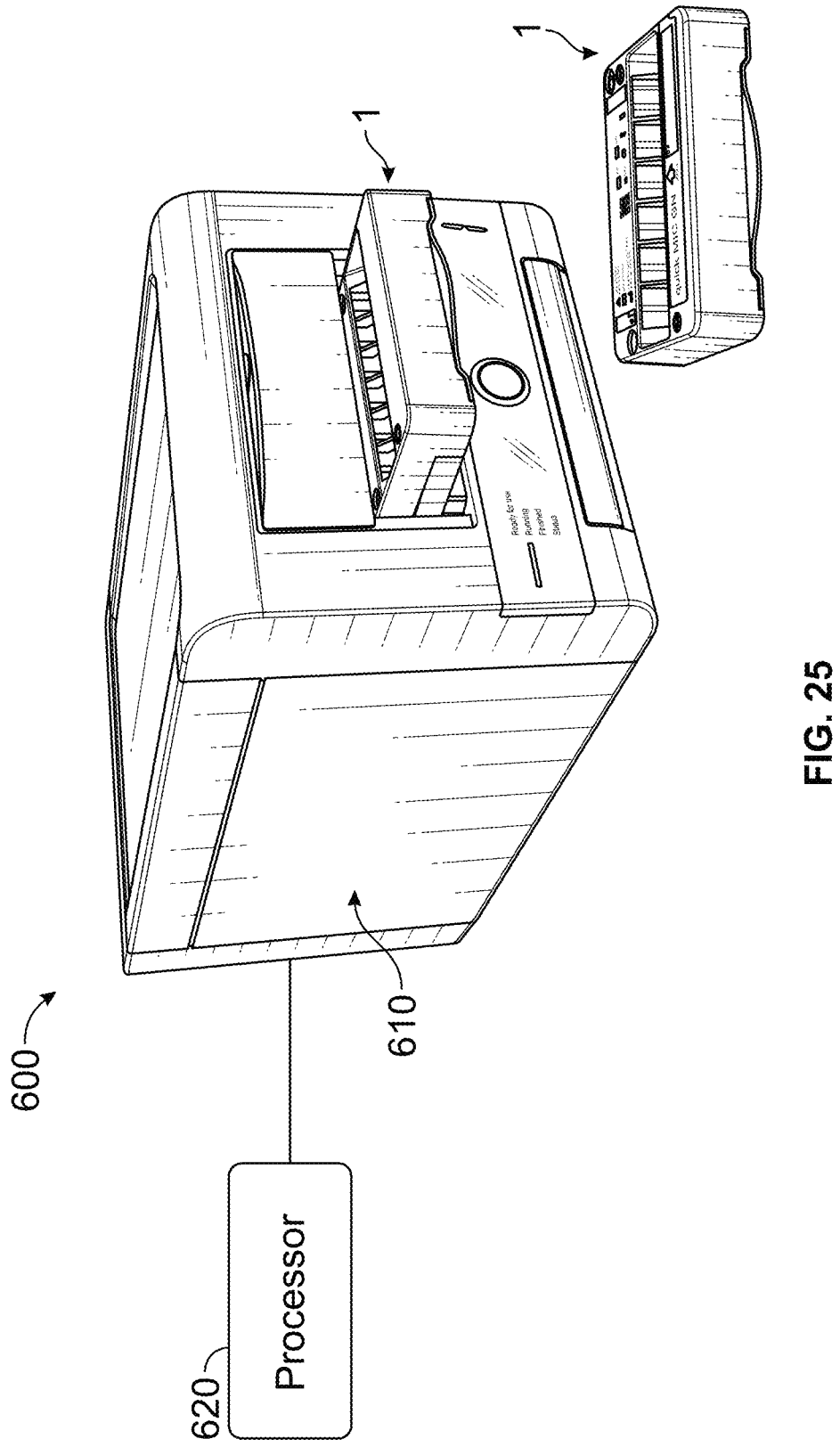

FIG. 17 is a close up of a portion of a cassette half following application of a short pressure pulse according to an embodiment;

FIG. 18 is bottom view of a cassette assembly in connection with application of a long pressure pulse according to an embodiment;

FIG. 19 is a top view of cassette halves and slider in connection with application of a long pressure pulse (top panel) and a cross-sectional view along the line C-C (bottom panel) according to an embodiment;

FIG. 20 is a cross-sectional view along the line C-C in FIG. 19 following application of a short under pressure pulse according to an embodiment;

FIG. 21 is a side view of a cassette half and a slider in a sample filling position according to an embodiment;

FIG. 22 is a side view of a cassette half and a slider in a flow position according to an embodiment;

FIG. 23 is a side view of a cassette half according to an embodiment;

FIG. 24 is a bottom view of a cassette assembly during operation to establish a concentration gradient through a 3D culture matrix inside a test chamber according to an embodiment; and FIG. 25 is a schematic overview of a system for determining a response of microorganisms to test agents according to an embodiment.

DETAILED DESCRIPTION

Throughout the drawings, the same reference numbers are used for similar or corresponding elements.

The embodiments generally relate to cassette assemblies for fluidic systems, and in particular to such cassette assemblies that can be used to determine a response of microorganisms to test substances or agents.

It has been concluded that fluidic systems, such as microfluidic systems, can be designed to be particularly suitable to monitor or determine the response of microorganisms to various test agents. In more detail, such fluidic systems, having a test chamber with a three-dimensional (3D) culture matrix containing a culture of the relevant microorganisms, provide an efficient tool to quickly determine the response of the microorganisms to the test agent or indeed to any combination of multiple test agents.

Such fluidic systems have key features that make them a very efficient tool. Firstly, a steady-state gradient of the relevant test agent can quickly and accurately be established over at least a portion of the 3D culture matrix. This means that a continuous range of test agent concentrations is established from a high concentration at one of the end portions or sides of the 3D culture matrix down to a low or zero concentration at another end portion or side of the 3D culture matrix. Hence, a continuous range of concentrations of the test agent can be tested. This is in clear contrast to prior art techniques where one or at most a few predefined concentrations but not any continuous range of concentrations can be tested. Accordingly, a more exact determination of, for instance, minimum inhibitory concentration (MIC) of an antibiotic can be made.

Secondly, the microorganisms are cultured in a 3D culture matrix. Accordingly, the microorganisms are allowed to grow in three dimensions. This in turn provides a significant difference between areas of the 3D culture matrix where viable and growing microorganisms are present and areas with cell death or low growth. Accordingly, the embodiments provide an enhanced signal-to-noise ratio. Hence, it is much easier to differentiate between different areas or zones in the 3D culture matrix as compared to growing microorganisms as a biofilm on a two-dimensional (2D) surface where fewer microorganisms can be grown and, thus, lower detection signals are generated.

A gradient of the test agent can quickly be established over at least a portion of the 3D culture matrix. This together with the possibility of microorganism growth in three dimensions enables reading the response of the microorganisms to the test agent in a very short time, generally within one or at most a few hours. This should be compared to several of the prior art techniques, typically requiring incubation overnight.

The present invention relates to a cassette assembly for a fluidic system and that is designed to house 3D culture matrices. The cassette assembly can therefore be used in the fluidic system to monitor and determine responses of microorganisms to test agents. A typical application of the cassette assembly is to analyze the susceptibility of a biological sample, such as a blood sample, from a patient suffering from a bacterial infection, such as sepsis, to different antibiotics and to determine the MIC of each of the antibiotics for the bacteria in the biological sample in a short period of time, typically within 1-4 hours.

The cassette assembly is preferably in the form of a disposable cassette assembly preloaded with test agents, such as antibiotics, into which the biological sample is loaded. The fluidic system in addition comprises an analysis instrument that is used to monitor and analyze, preferably optically monitor and analyze, bacterial growth while the biological sample is exposed to gradients of antibiotics.

The cassette assembly 1, see FIGS. 1 to 6, is composed of four main components, two cassette halves 200A, 200B, a slider 300 and a cover 100. The cassette halves 200A, 200B comprise inlet ports 210, 211 for the biological sample and a liquid and connection ports 212 for a pressure interface. The slider 300 comprises test chambers 302 in the form of through holes through the thickness of the slider 300. The 3D culture matrices will be formed in these test chambers 302 and microorganism growth and response to test agents will be monitored and analyzed. The cover 100 is employed to keep the main components together and has a supporting function.

The cover 100 has a lid 105 and four side walls 101, 102, 103, 104 extending from the lid 105 and comprising two end walls 102, 104 and two longitudinal walls 101, 103. The two end walls 102, 104 preferably comprise a respective window 106 that is configured to receive end walls 201, 203 of the two cassette halves 200A, 200B as shown in FIG. 4.

Figure 4:
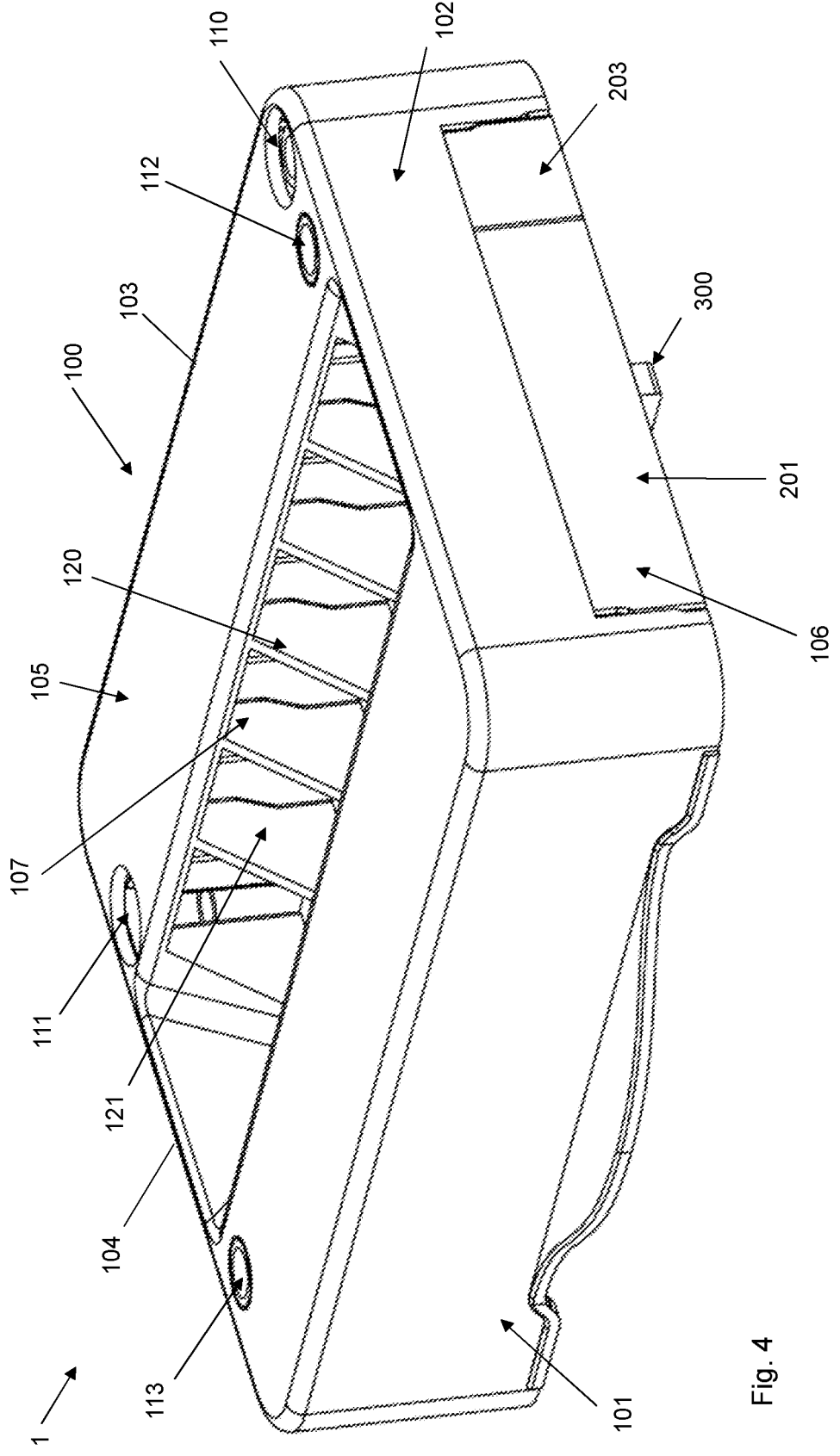
FIG. 4 is an illustration of a cassette assembly according to an embodiment.

The lid 105 of the cover 100 comprises openings 110, 111, 112, 113 positioned to be aligned with inlet and connection ports 210, 211, 212 in the two cassette halves 200A, 200B when the main components are assembled together as shown in FIG. 4. The lid 105 also comprises a central opening or window 107 providing visual access through the cover 100 to the slider 300 and the test chambers 302 provided therein. In a preferred embodiment, supporting structures 120 extend from the bottom surface of the lid 105 and supports a slider cover 122 configured to be aligned with and covering the slider 300 in the cassette assembly 1. The supporting structures 120 are arranged at the lid 105 with spaces between adjacent supporting structures 120 to form windows 121 allowing visual access to reservoirs 240 in the cassette halves 200A, 200B in the cassette assembly 1. The slider cover 122 comprises openings or windows 123 that are aligned with the test chambers 302 in the slider 300 to provide visual access through the slider cover 122 and into the test chambers 302.

In an embodiment, snap-fit connectors may be used to interconnect the cover 100 with the cassette halves 200A, 200B with the slider 300 sandwiched between the first and second cassette halves 200A, 200B. In such a case, the cover 110 may comprise at least one snap-in area or through hole, such as in each of its end walls 102, 104 and/or longitudinal walls 101, 103. The first and second cassette halves 200A, 200B may then comprise a protruding structure or lip configured to enter the snap-in area or through hole in the cover 100 to achieve a snap-fit lock, preferably a cantilever snap-fit lock.

In an embodiment, the cover 100 may comprise two snap-in areas or through holes positioned one on top of the other. In such an embodiment, the cover 100 can be locked to the first and second cassette halves 200A, 200B in two different positions, preferably corresponding to a transportation position, see FIG. 7, and a loading position, see FIGS. 4 and 8. In such a case, the cassette assembly 1 may be delivered in the transportation position with the protruding structures or lids of the first and second cassette halves 200A, 200B in the lowest of the snap-in areas or through holes in the cover 100. This means that the components of the cassette assembly 1 are preferably interlocked also during transport to thereby prevent the components from falling apart. In the loading position, the cover 100 is pressed downwards thereby causing the protruding structures or lids of the first and second cassette halves 200A, 200B to enter the uppermost of the snap-in areas or through holes in the cover 100 to thereby keep the components interlocked in this loading position.

In the embodiments above, the snap-fit connector has been described with the snap-in area in the cover 100 and the protruding structures or lids in the first and second cassette halves 200A, 200B. In another embodiment, the snap-in areas are instead in the first and second cassette halves 200A, 200B with the matching protruding structure or lids in the cover 100.

Also other solutions of interlocking the components of the cassette assembly 1, preferably in two different positions corresponding to the transportation and loading positions, are possible and can be used instead of snap-fit connectors.

The slider 300 comprises two through holes 301, each provided in connection with a respective end of the slider 300. These through holes 301 form part of a fluidic system to enable liquid to flow between the cassette halves 200A, 200B and through the slider 300. These two through holes 301 are arranged to be aligned with respective openings 254 in front walls 204 of the cassette halves 200A, 200B as is more clearly shown in FIG. 23. The end sides of the slider 300 preferably comprise a projection 303 that can be slid into a matching indentation in a side wall 203 of the cassette halves 200A, 200B to align the slider 300 relative to the cassette halves 200A, 200B. The slider 300 can preferably be vertically moved relative to the cassette halves 200A, 200B between a sample filling position (FIG. 21) and a flow position (FIG. 22) as is further described herein.

The two cassette halves 200A, 200B are preferably identical with the exception that one of the cassette halves 200A is preferably preloaded with test agents, such as antibiotics, in reservoirs 240, whereas the other cassette half 200B preferably lacks such test agents. In an embodiment, one of the two cassette halves 200A, 200B also comprises a plug, membrane or tape in the liquid inlet to prevent leakage through the circumferential channel during filling as is further described herein. In the following, a cassette half 200 is described in more detail and this description applies to both cassette halves 200A, 200B unless otherwise indicated.

A cassette half 200 comprises end sides or walls 201, 203, of which one is preferably longer than the other one. One of the end walls 203 comprises a projection 206 configured to be slid into a matching groove 205 in an end wall 201 of the other cassette half. The cassette half 200 also comprises a back wall 202 and a front wall 204 configured to face the slider 300. The front wall 204 comprises openings or connections 254 that are to be aligned with through holes 301 in the slider 300 to provide a circumferential liquid flow in a fluidic system 215. The front wall 204 also comprises multiple pairs of openings or interfaces 252, 253, preferably one pair per test chamber 302 in the slider 300. Each such pair comprises an upper opening or interface 252 to be used for a liquid flow and a lower opening or interface 253 to be used for a sample flow. Each pair of openings or interfaces 252, 253 and the opening or connection 254 and liquid enclosing interface 255 in the front wall 204 preferably comprises a respective gasket or seal 251 circumferentially enclosing the openings, interfaces or connections 252, 253, 254, 255. The gaskets or seals 251 are configured to contact the main surfaces of the slider 300 and thereby be pressed between the slider 300 and the front wall 204 to form a liquid tight connection.

Figure 16:
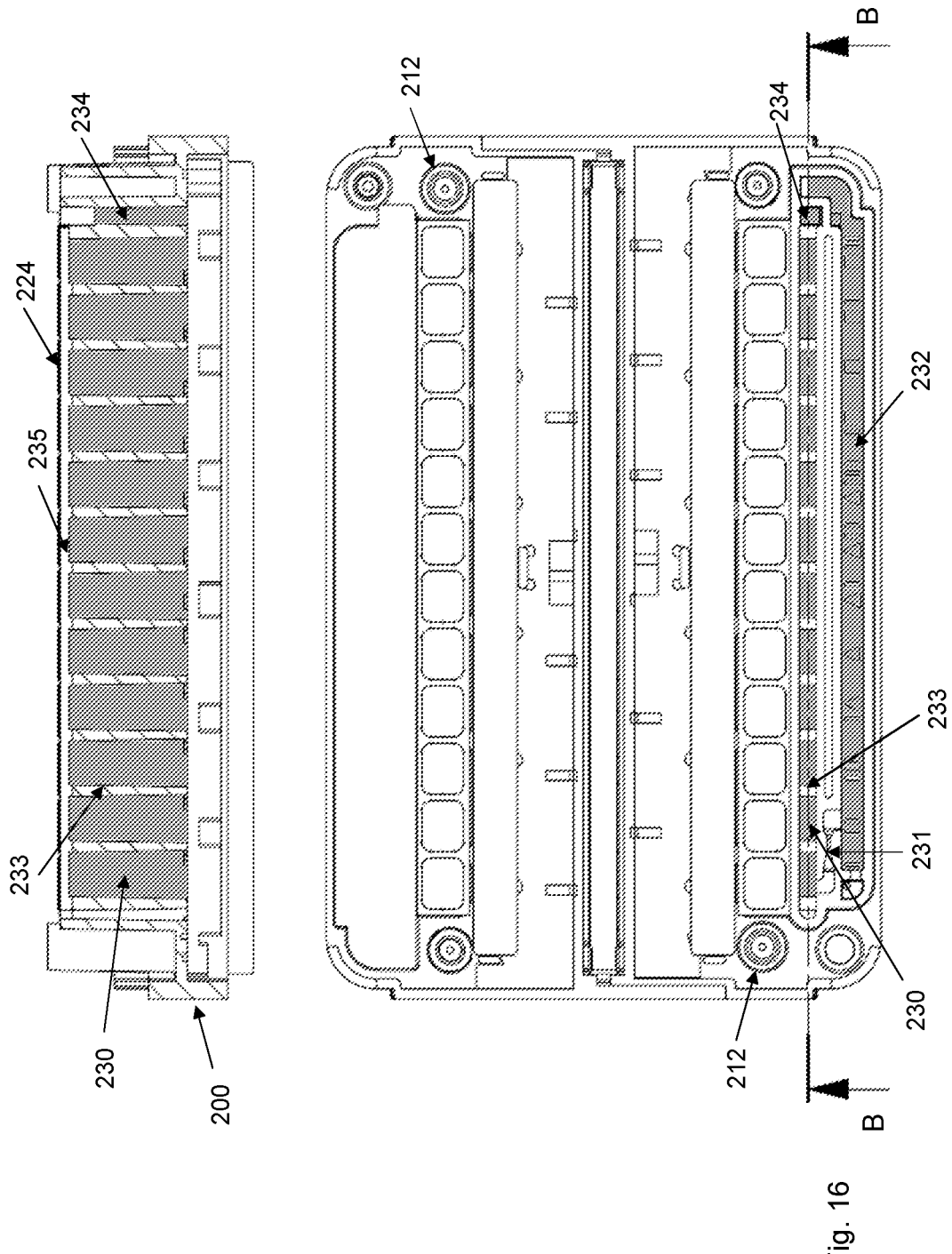
FIG. 16 is a top view of cassette halves and slider following application of a short pressure pulse (bottom panel) and a cross-sectional view along the line B-B (top panel) according to an embodiment.

The cassette half 200 also comprises the previously mentioned inlet ports 210, 211 for the biological sample and a liquid and connection ports 212 for a pressure interface of the analysis instrument forming part of the fluidic system. The cassette half 200 further comprises a number of waste tanks 230 separated by a respective wall 233. There is a head space 235 above the waste tanks 230 and the walls 233 as more clearly shown in FIGS. 12 and 16. The cassette half 200 preferably comprises one waste tank 230 per test chamber 302 in the slider 300. The waste tanks 230 are in fluid connection with the inlet port 210 in at least one of the cassette halves 200A, 200B through a fluidic system 215 shown in FIG. 10 running along the end walls 201, 203 and the back wall 202 of the cassette half 200. As a consequence, the fluidic system 215 forms a circumferentially continuous channel in the cassette assembly 1 formed by a first channel part in one of the cassette halves 200A, 200B, the through holes 301 in the slider 300 and a second channel part in the other of the cassette halves 200A, 200B. The fluidic system 215 also comprises a serpentine channel 216 per cassette half 200 interconnecting the circumferential continuous channel with the waste tanks 230.

The waste tanks 230 are in fluid connection with an excessive liquid tank 232 through a vertical outlet channel 234. There is also a fluid connection between the waste tanks 230 and the excessive liquid tank 232 in the form of a narrow channel 231 acting as an air valve between the waste tanks 230 and the excessive liquid tank 232. In an embodiment, the excessive liquid tank 232 comprises markings 237 in its bottom to identify the respective sets of waste tanks 230, reservoirs 240 and test chambers 302.

The cassette half 200 further comprises a number of reservoirs 240, preferably one such reservoir 240 per waste tank 230. Each waste tank 230 is then in fluid connection with a respective reservoir 240 through a channel 242 extending from the waste tank 230, preferably passing a restrictive filter 241, turning at the slider 300 and then continuing to the reservoir 240 as shown in FIG. 18. The reservoirs 240 in one of the cassette halves 200A, 200B are preferably prefilled with a respective test agent, such as freeze dried antibiotic, whereas the reservoirs 240 in the other of the cassette halves 200A, 200B preferably lack the test agents.

Figure 1:
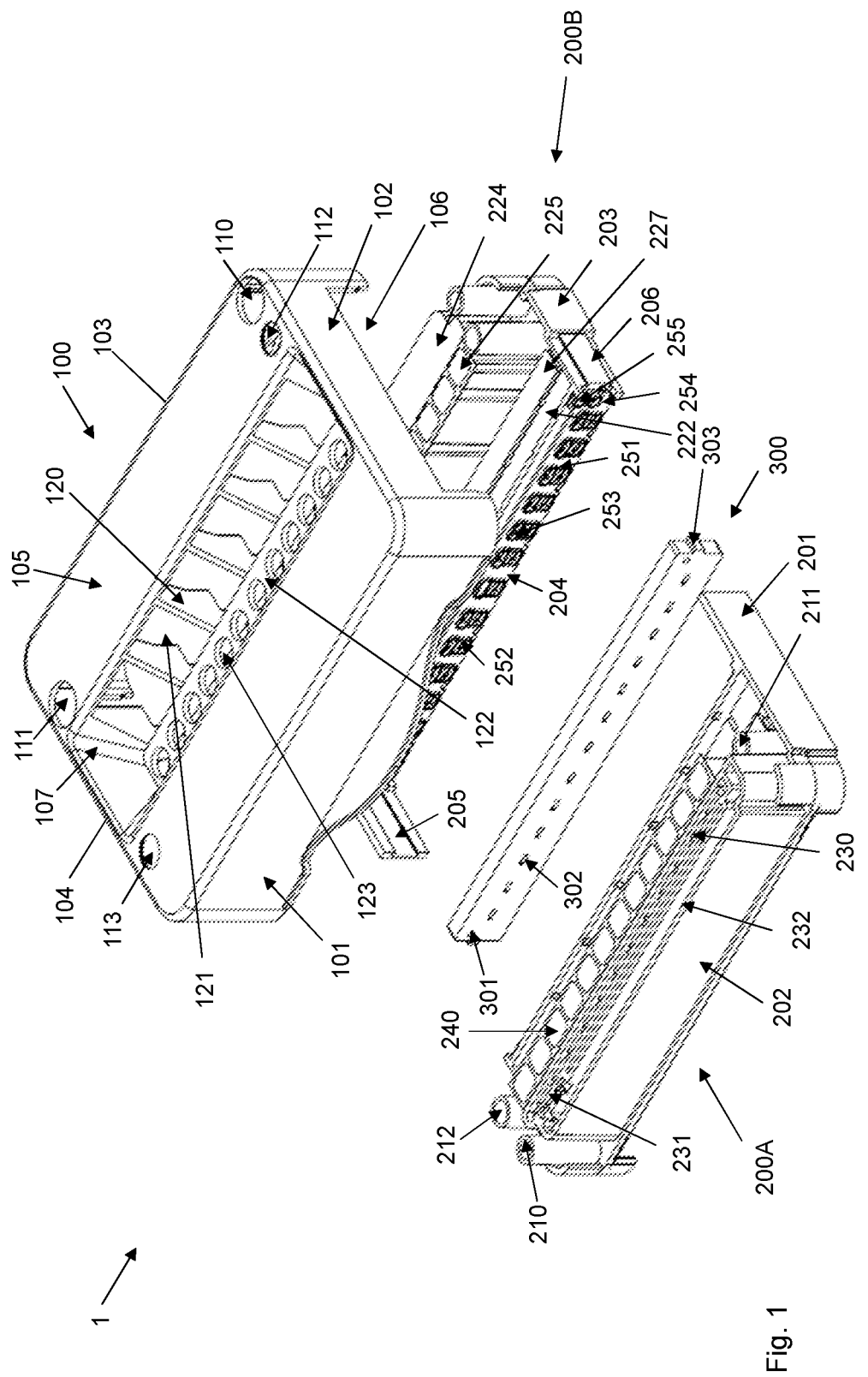
FIG. 1 is an illustration of a cassette assembly and its main components according to an embodiment.
Figure 2:
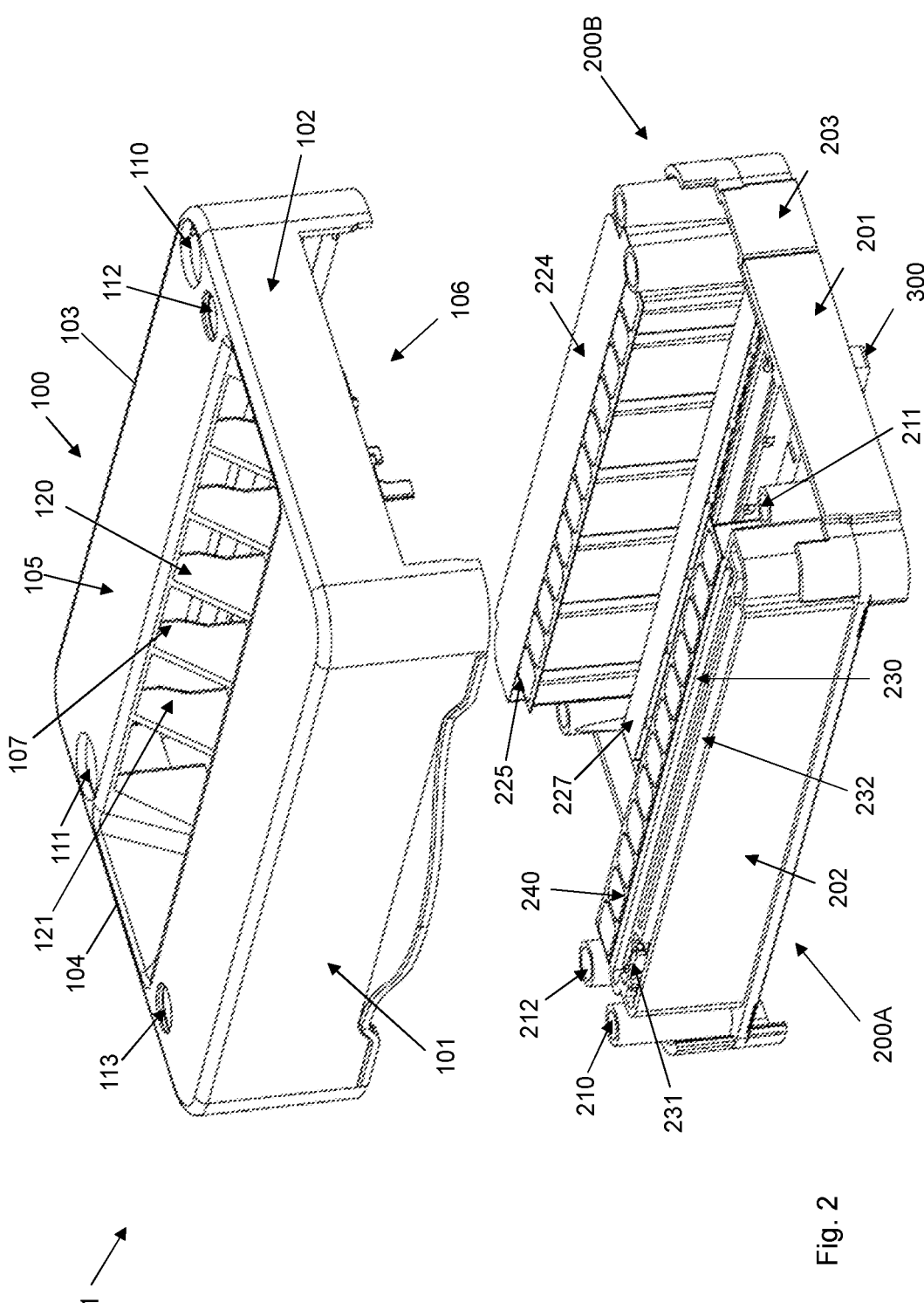
FIG. 2 is an illustration of a cassette assembly with cassette halves and slider assembled according to an embodiment.
Figure 3:
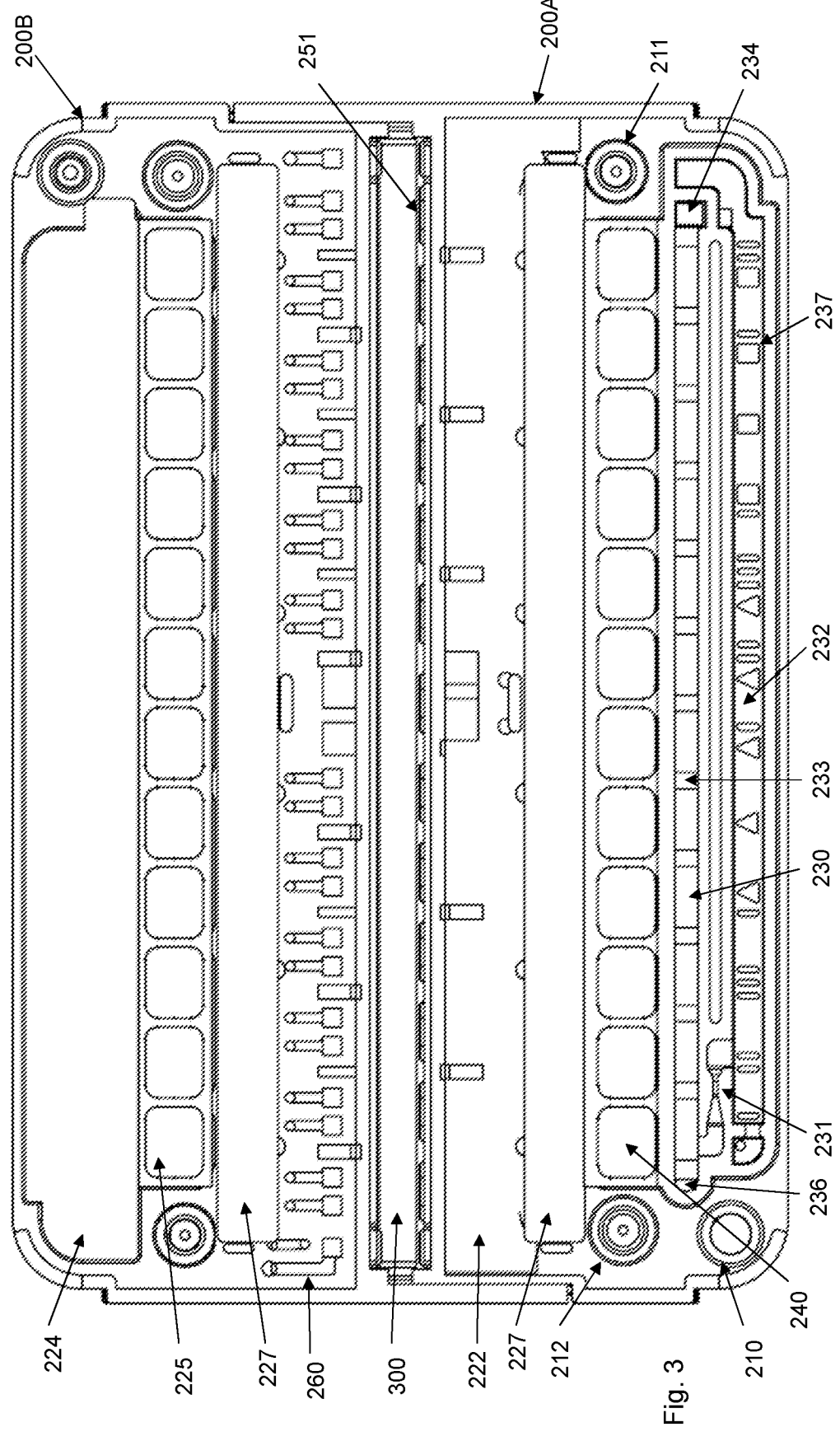
FIG. 3 is a top view of cassette halves and slider assembled according to an embodiment.

FIG. 1 illustrate the four main components of the cassette assembly 1 as separate components prior to interconnecting the components. FIG. 2 illustrates the cassette assembly 1 with the cassette halves 200A, 200B interconnected and with the slider 300 sandwiched between the front walls 204 of the cassette halves 200A, 200B. FIG. 3 illustrates the interconnected cassette halves 200A, 200B and slider 300 as seen from above. FIG. 4 illustrates the cassette assembly 1 with the cover 100 attached to the cassette halves 200A, 200B in a loading position, i.e., with the cover 100 pushed down towards the cassette halves 200A, 200B so that the end walls 201, 203 of the cassette halves 200A, 200B enter the window 106 in the end wall 102 of the cover 100.

Figure 5:
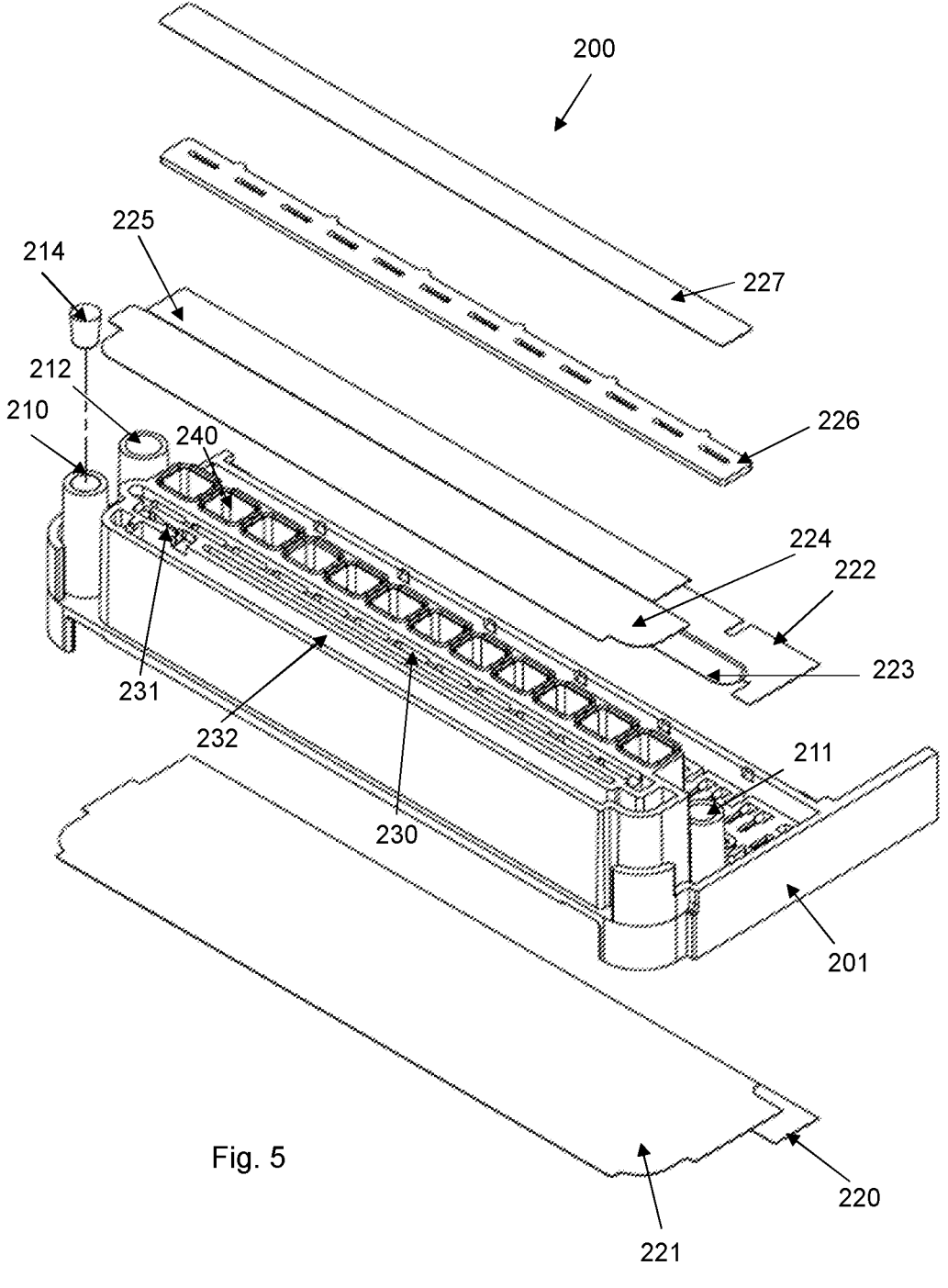
FIG. 5 is an illustration of a cassette half together with various tapes, membranes and covers according to an embodiment.
Figure 6:
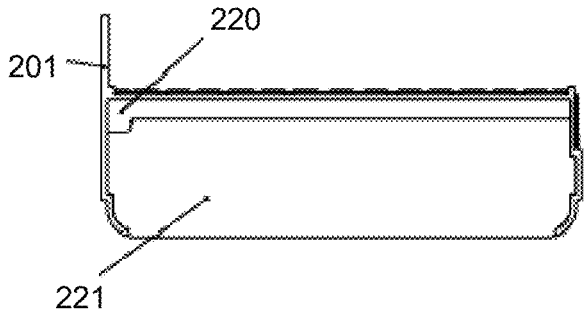
FIG. 6 is an illustration of a cassette half together with various tapes, membranes and covers as seen in a bottom view (top panel), a side view (middle panel) and a top view (bottom panel) according to an embodiment.
Figure 6:
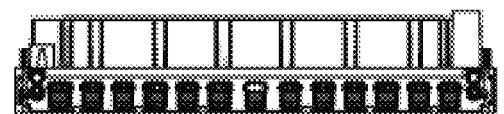
Figure 6:
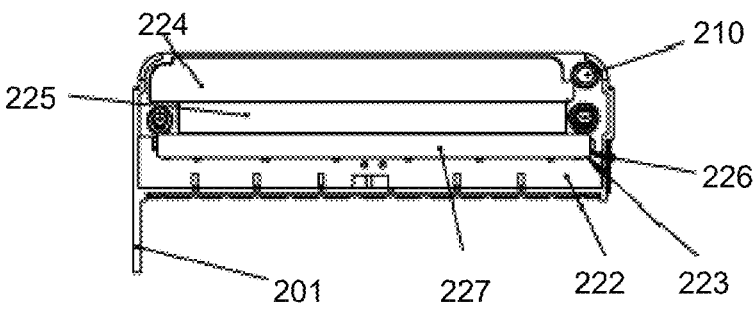

FIGS. 5 and 6 illustrate a cassette half 200 together with various tapes, membranes and covers according to an embodiment. FIG. 6 illustrates the tapes, membranes and covers attached to the cassette half 200 as seen in a bottom view (top panel), a side view (middle panel) and a top view (bottom panel). In this embodiment, two bottom tapes 220, 221 are attached to the underside of the cassette half 200 to enclose the fluidic components and channels in the cassette half 200, see top panel of FIG. 6. A first top tape 224 covers the waste tanks 230 and excessive liquid tank 232. A membrane 223, such as a polyethersulfone (PES) membrane, is interposed between a shoe tape 227 and a restriction bar 226. In another embodiment, the membrane 223 is omitted as is further described herein. Furthermore, also the shoe tape 227 and the restriction bar 226 may be omitted, which is further discussed herein. A membrane 225, such as a polytetrafluoroethylene (PTFE) membrane, is used to cover the reservoirs 240. A second top tape 222 is designed to cover the fluidic components and channels in the cassette half 200.

Figure 7:
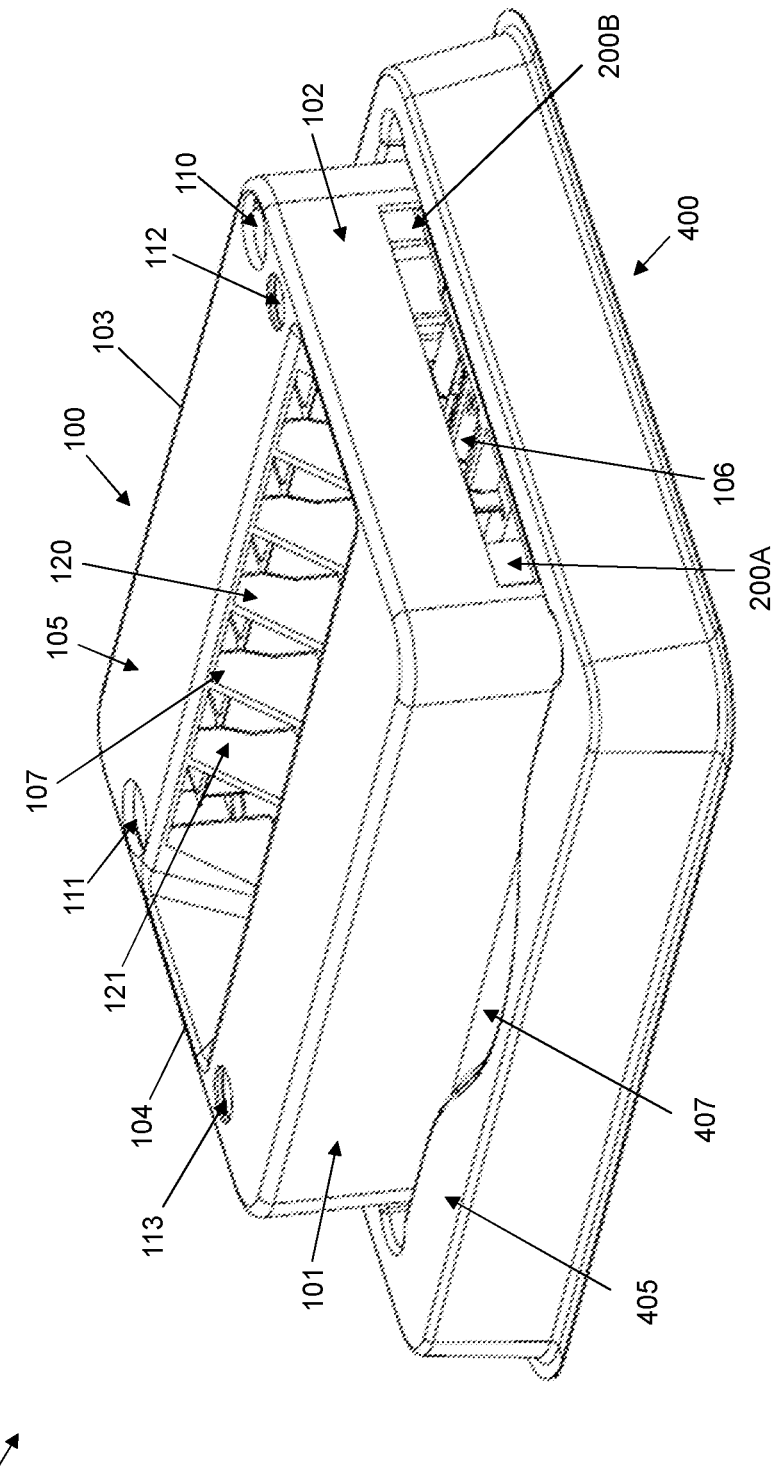
FIG. 7 is an illustration of a cassette assembly positioned in a cassette tray in a transportation position according to an embodiment.

In an embodiment, the cassette assembly 1 is shipped with cover 100 in a transport position as shown in FIG. 7, where the cover 100 keeps the main components together but prevents compression of the gaskets or seals 251 between the cassette halves 200A, 200B and the slider 300. In an embodiment, the cassette assembly 1 is also positioned in a cassette tray 400 during transportation as shown in the figure. The cassette tray 400 then comprises an opening 407 in its top surface 405 into which the cassette assembly 1 inserted.

Figure 8:
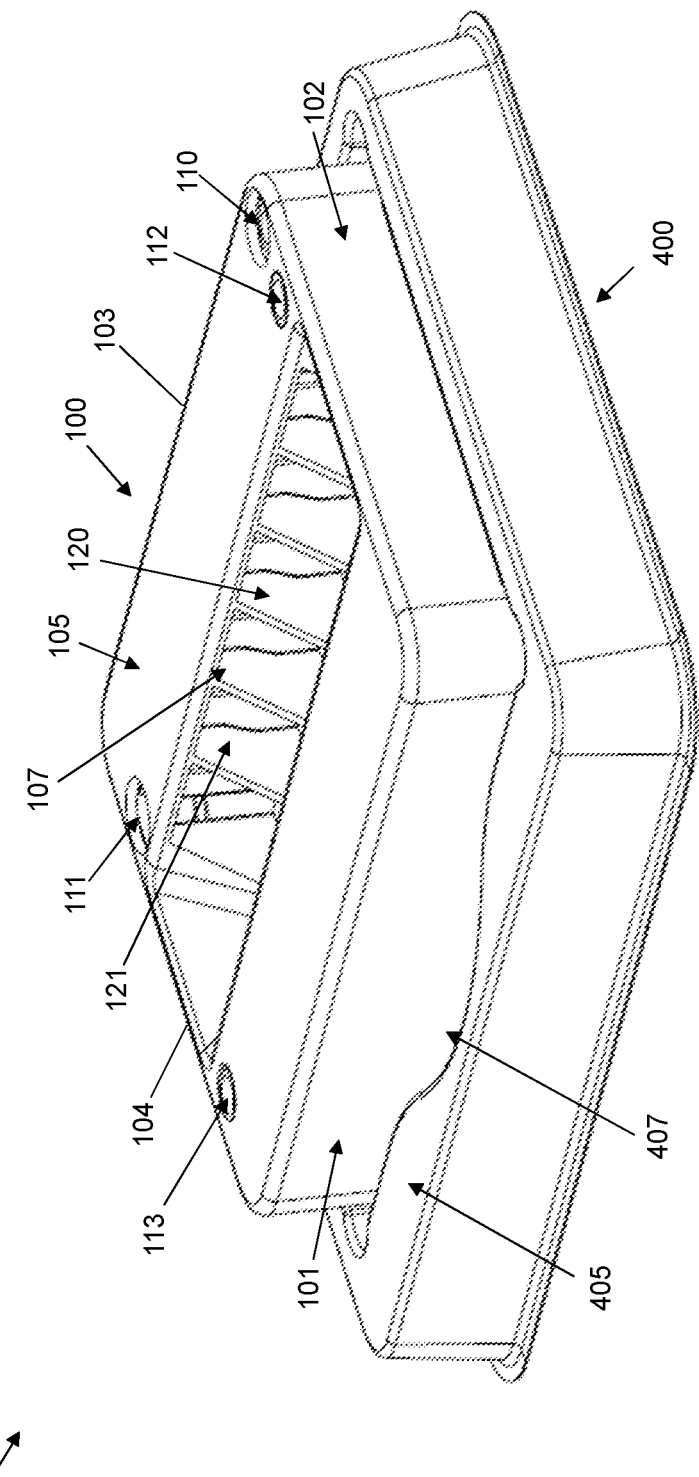
FIG. 8 is an illustration of a cassette assembly positioned in a cassette tray in a loading position according to an embodiment.

The user then preferably pushes the cover 100 down into the loading position shown in FIG. 8. This causes a compression of the gaskets or seals 251 between the front walls 204 of the cassette halves 200A, 200B and the slider 300 to thereby keep the cassette assembly 1 tight to avoid leaks in the points of contact between the cassette halves 200A, 200B and the slider 300 when the sample and the liquid are injected.

Figure 9:
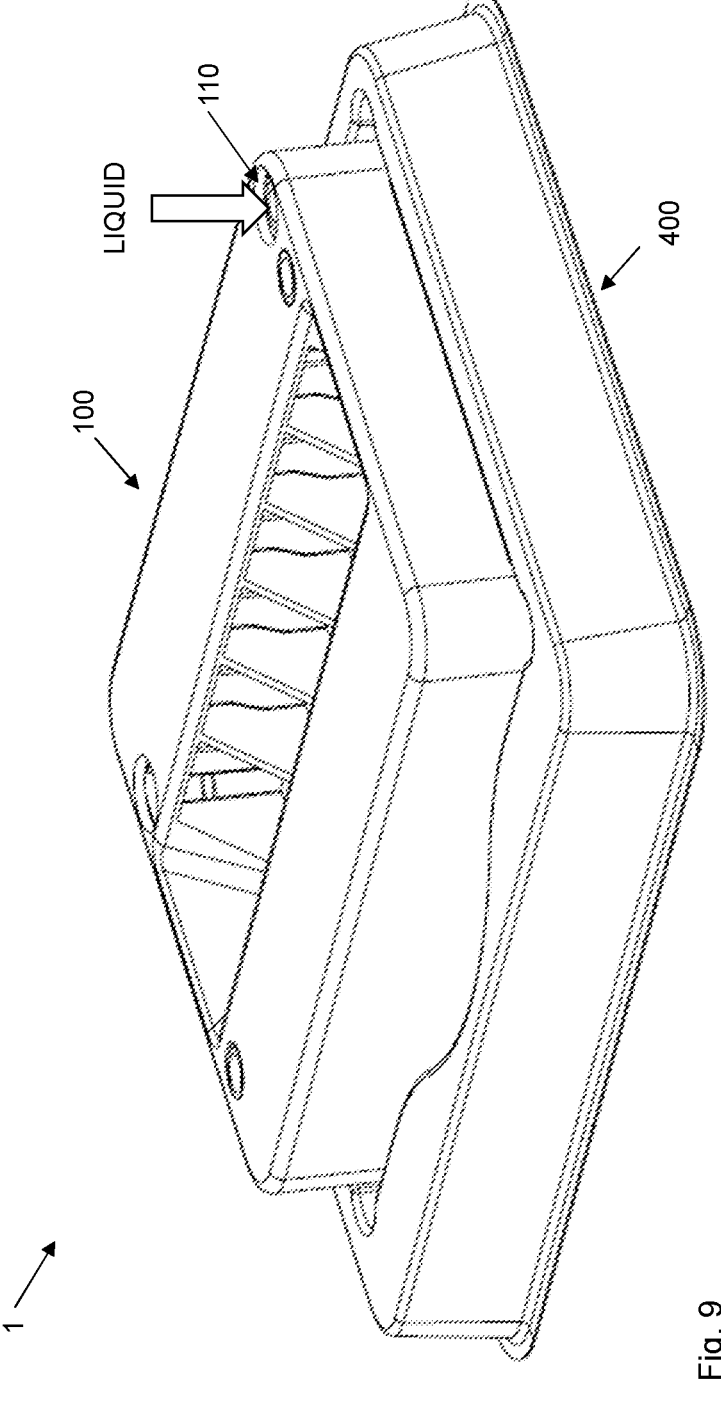
FIG. 9 is an illustration of a cassette assembly in connection with liquid loading according to an embodiment.

FIG. 9 illustrates the cassette assembly 1 when liquid, such as water, an aqueous solution, a buffer solution, a culture medium, etc., is loaded through an opening 110 in the cover 100 positioned to be aligned with an inlet port 210 in one of the cassette halves 200A, 200B. The corresponding inlet port 210 in the other cassette half is preferably plugged with a plug 214 as shown in FIG. 5 or could be sealed with a membrane or tape. The injection of liquid through the opening 110 allows filling of the waste tanks 230 in both cassette halves 200A, 200B in a first step followed by transferring metered volumes of the liquid from the waste tanks 230 into the reservoirs 240.

Figure 10:
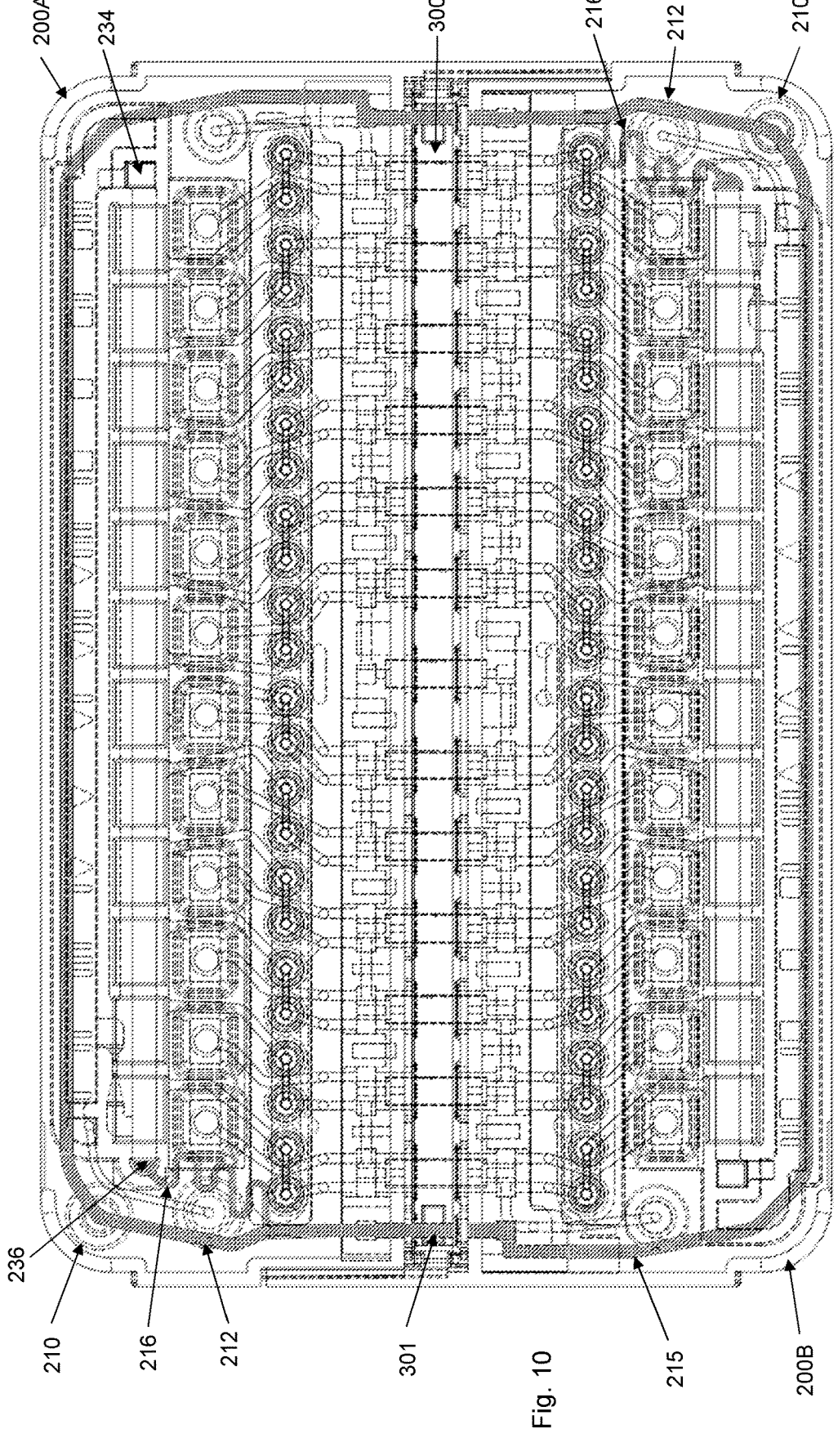
FIG. 10 is a bottom view of a cassette assembly in connection with liquid loading according to an embodiment.

As is more clearly shown in FIG. 10, the liquid first flows through a circumferential channel 215 connecting the two cassette halves 200A, 200B. The liquid then flows through two serpentine and narrow channels 216, which divide the injected liquid into two equal volumes, one for each cassette half 200A, 200B. The serpentine channels 216 present a significantly higher flow resistance as compared to the circumferential channel 215. Accordingly, once the liquid is injected through the opening 110 and the inlet port 210, the liquid first fills up the circumferential channel 215 before entering the serpentine channel 216. This design of the serpentine channels 216 and the circumferential channel 215 achieves a division of the injected liquid into two equal volumes, one for each cassette half 200A, 200B. In addition, the serpentine channels 216 enable a substantially timed filling of the two series of waste tanks 230 in the two cassette halves 200A, 200B with substantially the same flow rates in both cassette halves 200A, 200B.

Figure 11:
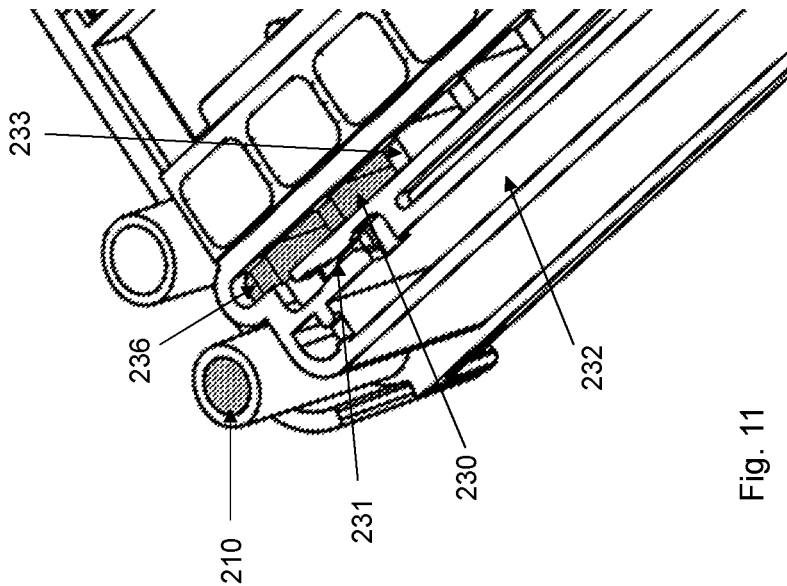
FIG. 11 is a close up of a portion of a cassette half in connection with liquid loading according to an embodiment.

From the respective serpentine channel 216, the liquid fills up, via a vertical inlet channel 236, a series of waste tanks 230 connected via a head space 235 as shown in FIG. 11. Thus, the vertical inlet channel 236 is connected to the serpentine channel 216 in connection with its lower end and the vertical inlet channel 236 is connected to the series of waste tanks 230 in connection with its upper end.

Figure 12:
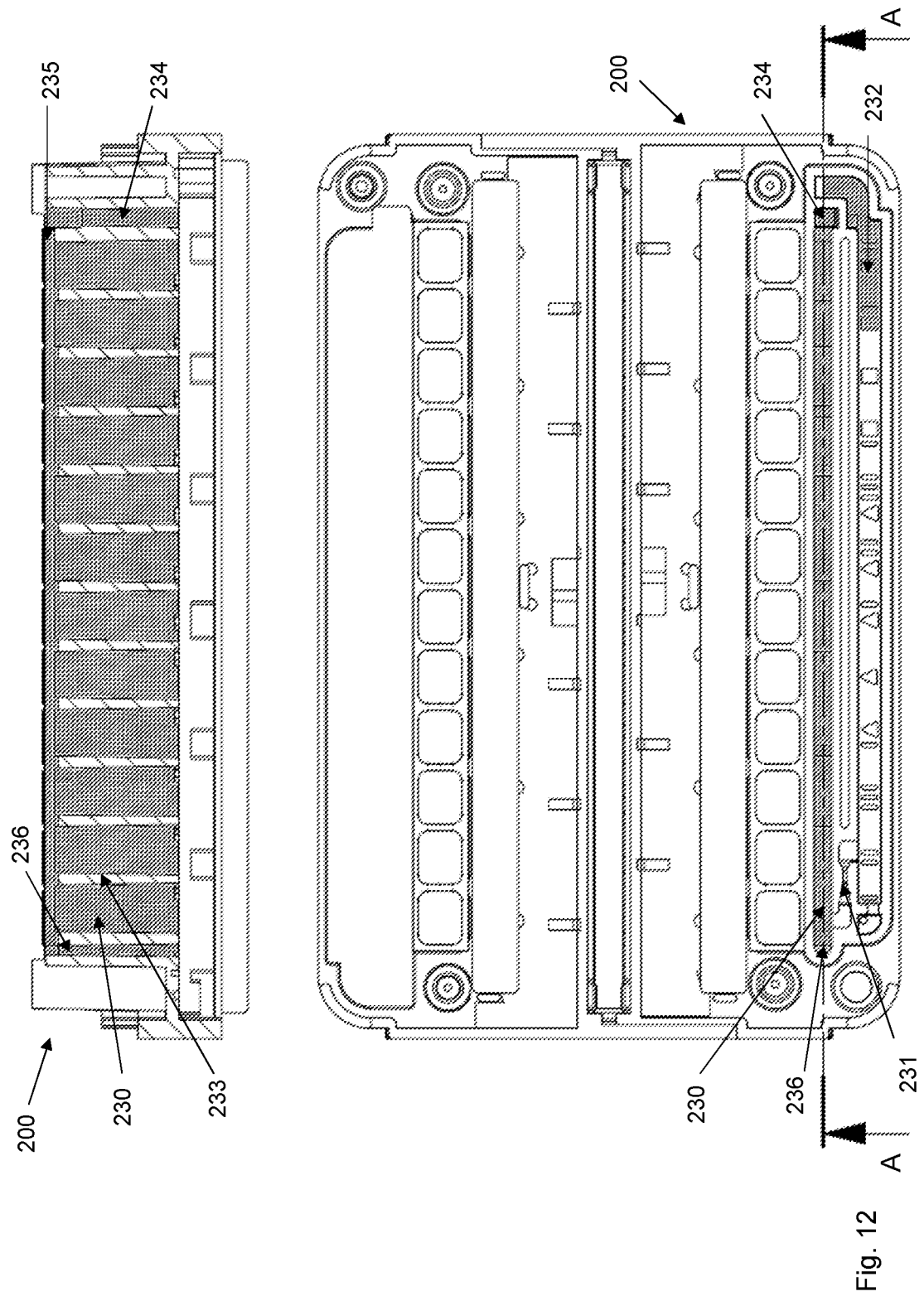
FIG. 12 is a top view of cassette halves and slider in connection with liquid loading (bottom panel) and a cross-sectional view along the line A-A (top panel) according to an embodiment.

The waste tanks 230 are separated by walls 233 to form a series of waste tanks 230 that are in fluid connection with each other through the head space or volume 235 present between the walls 233 and the top tape 224. The waste tanks 230 become filled one after each other. Hence, liquid coming from the serpentine channel 216 enters a first waste tank 230 and starts filling this first waste tank 230. Once the first waste tank 230 is full liquid flows over the wall 233 separating the first waste tank 230 and a second waste tank through the head space 235 and starts filling the second waste tank 230. This process continues until all waste tanks 230 are full with liquid as shown in FIG. 12. Any excessive liquid escapes into an excessive liquid tank 232 via a vertical outlet channel 234.

The head space 235 of the waste tanks 230 is also connected to the excessive liquid tank 232 via an air valve 231 in the form of a narrow channel. The air valve 231 presents a higher flow resistance as compared to the vertical outlet channel 234. This means that during filling, liquid will not penetrate through the air valve 231 but rather flow between waste tanks 230 and then, when the waste tanks 230 are full, enter the excessive liquid tank 232 via the vertical outlet channel 234 with the air valve 231 still remaining closed, i.e., no liquid passing there through.

Liquid may also flow from the waste tanks 230 into a portion of the liquid path or channel 242 interconnecting the waste tanks 230 and the reservoirs 240, see FIG. 18. However, any such escaping liquid at most goes to the restrictive filter 241 or slit. This restrictive filter 241 or slit has an opening pressure that is higher than any pressure that the escaping liquid may exert on the restrictive filter 241 or slit during the liquid filling procedure.

The excessive liquid tank 232 may comprise an absorbent material configured to absorb any excessive liquid entering the excessive liquid tank 232 from the waste tanks 230 and through the vertical outlet channel 234. The absorbent material may be in form of a sponge, film or other device made of an absorbent material, preferably a so-called super-absorbent material or superabsorbent polymer (SAP). The absorbent material may then be arranged in the excessive liquid tank 232 to have a length substantially corresponding to the length of the excessive liquid tank 232 or a portion of the length of the excessive liquid tank 232. The height of the absorbent material in the excessive liquid tank 232 is preferably selected so that the absorbent material does not reach the first top tape 224 covering the waste tanks 230 and excessive liquid tank 232 even when absorbing any liquid entering the excessive liquid tank 232. Hence, there is preferably an air gap between the top of the absorbent material and the first top tape 224 to enable opening of the air valve 231. This means that the height of the absorbent material is preferably less than the height of the excessive liquid tank 232.

The absorbent material can be made of any material capable of absorbing liquid entering the excessive liquid tank 232. In an embodiment, the absorbent material is made of SAP including, but not limited to, poly-acrylic acid sodium salt (sodium polyacrylate), polyacrylamide copolymer, ethylene maleic anhydride copolymer, cross-linked carboxymethylcellulose, polyvinyl alcohol copolymer, cross-linked polyethylene oxide, starch grafted copolymer of polyacrylonitrile. Also other absorbent materials could be used, including polyurethane (PUR).

The absorbent material in the excessive liquid tank 232 reduces the risk of any liquid in the excessive liquid tank 232 blocking the air valve 231, for instance if a user would tilt the cassette assembly 1 to cause any liquid in the excessive liquid tank 232 to contact the air valve 231 and remain in the air valve 231 once the cassette assembly 1 is once more levelled. Any such liquid captured in the air valve 231 might prevent or at least obstruct opening of the air valve 231.

Another advantage with the absorbent material is that it will keep the vertical outlet channel 234 interconnecting the waste tanks 230 and the excessive liquid tank 232 open, i.e., not full or at least partly full with liquid. Having an open vertical outlet channel 234 enables an even flow of liquid during operation (analysis) even if the air valve 231 would be unintentionally closed by a water droplet since air can then instead flow into the head space 235 through the vertical outlet channel 234 rather than through the air valve 231.

In very specific situations, such as dry ambient air, and depending on the material(s) of the components of the cassette assembly 1 and the type of liquid used, electrostatic forces may affect the transport of the liquid in the cassette assembly 1, and in particular the filling of the waste tanks 230. For instance, if such electrostatic forces are built up in the cover 100 and/or the first top tape 224, such forces may attract the liquid during filling causing at least some of the liquid to be transported along the underside of the first top tape 224 rather than flowing from waste tank 230 to waste tank 230. This may cause an incorrect filling of at least some of the waste tanks 230 in the cassette halves 200A, 200B.

The build-up of electrostatic forces in such very specific conditions can be avoided or at least significantly suppressed or inhibited according to various embodiments. For instance, the bottom side of the cover 100 could be sprayed with an electrically conductive composition to form a thin electrically conductive layer or film on at least the part of the cover 100 facing the waste tanks 230. Alternatively, or in addition, the cover 100 could be made of an electrically conductive material, such an electrically conductive plastic or polymer, or an electrically conductive additive could be added to the material of the cover 100 to get an electrically conductive cover 100. A further alternative is to provide a thin electrically conductive tape or film, such as an aluminum tape or film, between the waste tanks 230 and the first top tape 224. Yet other alternatives include providing a laminated first top tape 224 having an electrically conductive film attached to at least the surface of the first top tape 224 facing the waste tanks 230 or providing a coated first top tape 224 having an electrically conductive material coated or deposited onto at least the surface of the first top tape 224 facing the waste tanks 230. It would also be possible to use an electrically conductive first top tape 224. The above described solutions to prevent or at least inhibit build-up of electrostatic forces can be combined.

At this point either the sample is injected into the cassette assembly 1 or the head space 235 of the waste tanks 300 is cleared from liquid, which is further described herein.

Figure 13:
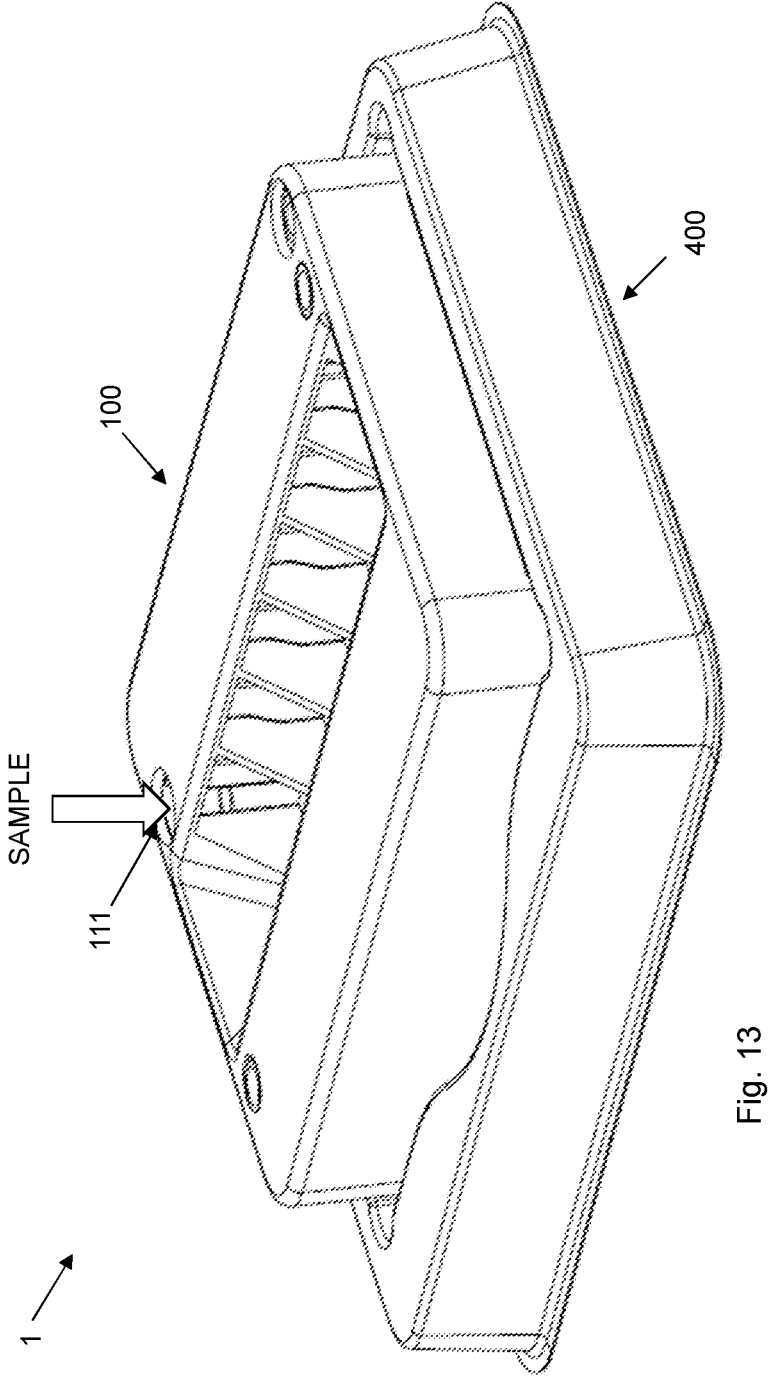
FIG. 13 is an illustration of a cassette assembly in connection with sample loading according to an embodiment.

The sample is injected into the cassette assembly 1 through an opening 111 in the cover 100 aligned with an inlet port 211 in one of the cassette halves as shown in FIG. 13. The sample is preferably a biological sample comprising a gel suspension that can be polymerized into a culture matrix in the respective test chambers 302 in the slider 300. The sample may optionally also comprise a culture medium allowing growth of any microorganisms, such as bacteria, in the culture matrix. The present invention can be used in connection with any type of culture matrix material known in the art and that can be injected into cassette assembly 1 and polymerized to form a solid 3D culture matrix. Additionally, the culture matrix once formed should preferably be transparent to allow visual inspection and visual access to the biological sample included therein.

Examples of suitable matrix material include agarose materials. An illustrative example of such an agarose material is ultra-low-gelling-temperature (ULGT) agarose. Other suitable materials include collagen materials, such as collagen I. Collagen I is well documented to support 3D cultures. Other gels that can be used include Engelbreth-Holm-Swarm (ECM) gels, such as Matrigel (BD Bioscience, Bedford, MA, USA) or hydrogels, including a mixture of phenylalanine (Phe) dipeptide formed by solid-phase synthesis with a fluorenylmethoxycarbonyl (Fmoc) protector group on the N-terminus, and Fmoc-protected lysine (Lys) or solely phenylalanine. However, any type of biocompatible matrix could be used as long as the matrix can be applied in soluble form and cast or polymerized to form a solid culture matrix.

Figure 14:
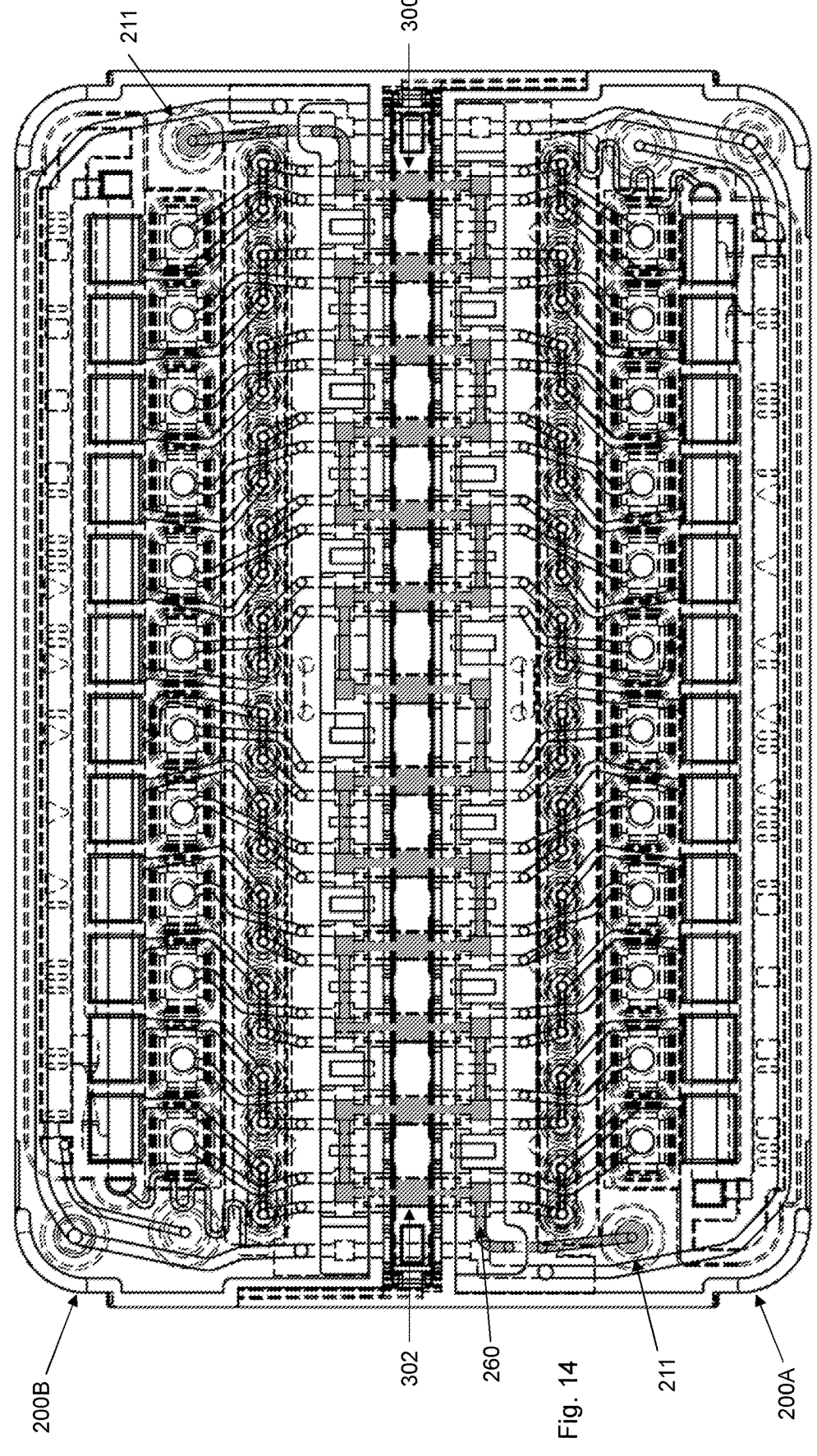
FIG. 14 is a bottom view of a cassette assembly in connection with sample loading according to an embodiment.

The sample flows, see FIG. 14, from the inlet port 211 in one of the cassette halves 200A, 200B through a channel system 260 and the test chambers 302 in the slider 300 in a meander pattern to fill respective test chamber 302 with the sample. The corresponding port 211 in the other cassette half 200B is preferably plugged with a filter, such as a filter plug, allowing air but not liquid to escape through the filter. This filter prevents any bacteria in the sample from escaping through the port 211 and thereby contaminating the outside of the cassette assembly 1.

Such a filter may, as an illustrative, but non-limiting, example, be a PFTE membrane allowing air to escape through the filter when dry. However, when the sample reaches the filter and wets it, the filter no longer lets air, or liquid, to escape through the filter. This can be used as a feedback signal indicating that no more sample should be injected into the inlet port 211.

The cassette assembly 1 is then preferably placed inside a refrigerator to initiate and finish the gel reaction of the sample and thereby formation of the solid 3D culture matrices in the test chambers 302 of the slider 300. The cassette assembly 1 is then brought out from the refrigerator and is now ready for running an analysis of the response of microorganisms, such as bacteria, present in the biological sample to test agents, such as antibiotics, preloaded, such as in freeze-dried form, in reservoirs 240 of one of the cassette halves 200A, 200B. At this point, the cassette assembly 1 can therefore be inserted into an analysis instrument of the fluidic system.

Figure 15:
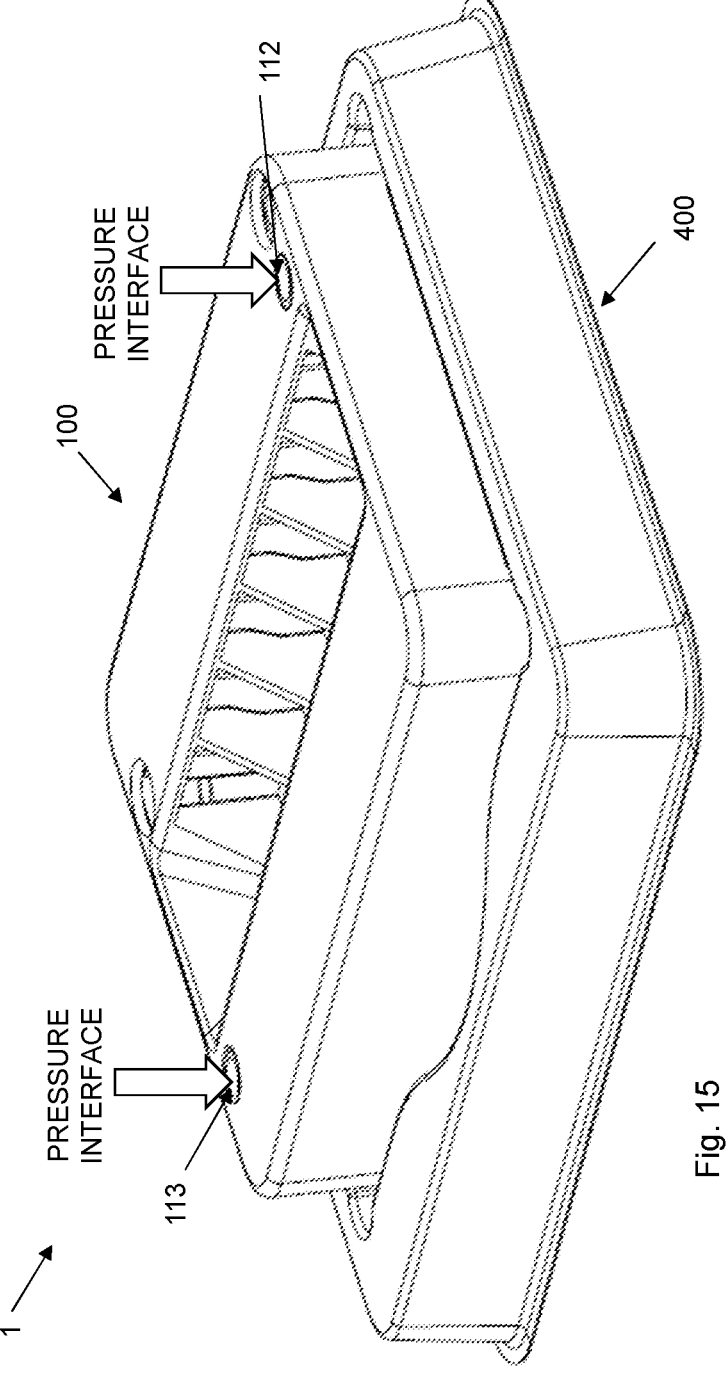
FIG. 15 is an illustration of a cassette assembly in connection with pressure application according to an embodiment.

Pressure interfaces, such as air pressure interfaces, are connected to openings 112, 113 in the cover 100 as shown in FIG. 15 and thereby to aligned connection ports 212 in the cassette halves 200A, 200B. A short over pressure pulse, typically a duration of one or few tens of a second, is introduced via the pressure interface to clear the head space 235 of the waste tanks 230 from liquid. This over pressure pulse opens up the air valve 231 connecting the head space 235 and the excessive liquid tank 232. The opening of the air valve 231 by the over pressure pulse causes drainage of the liquid in the head space 235 through the vertical outlet channel 234 and into the excessive liquid tank 232, see FIGS. 16 and 17. This operation divides the liquid in the waste tanks 230 into a number of separate and equal liquid volumes, one for each waste tank 230.

The air valve 231 is preferably in the form of a narrow channel interconnecting the head space 235 of the waste tanks 230 and the excessive liquid tank 232. The narrow channel presents a significantly higher flow resistance as compared to the vertical outlet channel 234. This means that during the serial filling of the waste tanks 230, any excess liquid will flow from the head space 235 and into the vertical outlet channel 234 rather than out through the air valve 231. The dimensions, in particular the cross-sectional dimensions, of the vertical outlet channel 234 relative to the dimensions of the narrow channel in the air valve 231 are preferably designed to create an under pressure by gravitation and capillary force that is sufficiently large to draw the excess liquid into the excessive liquid tank 232 but not that large to open the air valve 231 during the liquid filling stage.

As previously mentioned herein, the head space 235 could be cleared from liquid prior to sample filling. In such a case, gravitational forces acts on the liquid in the vertical outlet channel 234 causing a suction of air from the excessive liquid tank 232 through the air valve 231 and into the head space 235, i.e., opens the air valve 231. This causes drainage of the liquid in the head space 235 into the excessive liquid tank 232 through the vertical outlet channel 234 and thereby a separation of the liquid into equal volumes in the waste tanks 230.

Once the separate and equal volumes of liquid have been obtained in the waste tanks 230, a longer in time over pressure pulse, typically one or a few seconds, is applied to the waste tanks 230 via the excessive liquid tank 232 and the air valve 231. This pressure pulse presses the liquid out from the waste tanks 230 and into the reservoirs 240 via a liquid path or channel 242 as shown in FIG. 18 (showing liquid in only one of the waste tanks 230, reservoirs 240 and liquid paths or channels 242). The pressure pulse is sufficiently strong or high to open the restrictive filter 241 or slit arranged in the liquid path or channel 242 and thereby allow an emptying of liquid in the waste tanks 230 into the reservoirs 240.

The restrictive filter 241 or slit thereby has the function of preventing, during filling of the waste tanks 230, liquid from passing the restrictive filter 241 or slit in the liquid path or channel 242 but enable the liquid to flow through the liquid path or channel 242 past the restrictive filter 241 or slit once the opening pressure of the restrictive filter 241 or slit has been overcome by application of the pressure pulse.

In an embodiment, the restrictive filter 241 is formed by the membrane 223, such as PES membrane, and the restriction bar 226 shown in FIG. 5, which is closed by the shoe tape 227. In the case of a slit instead of the restrictive filter 241, the membrane 223 may be omitted. In such a case, the restriction bar 226 comprises the slits or the slits can be formed in the liquid path or channel 242. In this latter case, no restriction bar 226 is needed and can therefore be omitted together with the membrane 223 and the restrictive filter 241.

The reservoirs 240 are filled until the liquid reaches the membrane 225, preferably PTFE membrane, attached to the top of the reservoirs 240. The membrane 225 arranged on top of the reservoirs 240 is preferably designed to let out air but not an aqueous liquid. As a consequence, the membrane 225 guarantees that all reservoirs 240 are filled with the same volume of liquid.

FIG. 19 illustrates the reservoirs 240 filled with the same defined volumes of liquid. In a preferred embodiment, the reservoirs 240 in one cassette half 200A are preloaded with test agents, such as freeze dried antibiotics, which become dissolved into the liquid in the reservoirs 240. The reservoirs 240 in the other cassette half 200B preferably do not contain these test agents and will therefore only comprise the liquid at this point.

A short in time, typically in the range of one to a few seconds, under pressure pulse is applied to open up the membrane 225 for air flow. Thus, the under pressure pulse lets in a small volume of air 245 at the top of the reservoirs 240 as shown in FIG. 20. At this point, the slider 300 is moved upwards relative to the cassette halves 200A, 200B, from a sample filling position shown in FIG. 21 into a flow position shown in FIG. 22, to bring the 3D culture matrices present in the test chambers 302 in contact with the liquid paths or channels 241.

The relative movement between the slider 300 and the cassette halves 200A, 200B can be achieved either by pressing the cassette halves 200A, 200B and the cover 100 downwards with the bottom of the slider 300 resting on a surface or by pushing the slider 300 upwards relative to the cassette halves 200A, 200B and the cover 100.

The relative movement between the slider 300 and the cassette halves 200A, 200B additionally forms well defined ends or sides of the 3D culture matrices in the test chambers 302. Hence, the relative movement achieves a cutting of the gelled sample to form the 3D culture matrices. The newly cut ends or sides of the 3D culture matrices are further moved to be aligned with the liquid openings or interfaces 252 in the front walls 204 of the cassette halves 200A, 200B to thereby be exposed to the respective liquids filled in the two cassette halves 200A, 200B.

As is more clearly shown in FIG. 23, the cassette halves 200A, 200B have front walls 204 with two rows of openings or interfaces 252, 253, an upper sample filling row and a lower liquid flow row. The front wall 204 also has two cross flow connections or openings 254 coupling together the circumferential flow channel 215. The front wall 204 further comprises liquid enclosing interfaces 255 arranged to capture and enclose the minute liquid volume contained in the through holes 301 in the slider 300 when the slider 300 is moved relative to the cassette halves 200A, 200B to the position shown in FIG. 22. An optional center reaction or culture chamber act as the reference chamber 305 and has therefore no connection to the flow system. The figure also illustrates the gaskets or seals 251 around the interfaces and flow connections 252, 253, 254, 255.

In an embodiment, the gasket or seal 256 configured to be aligned with and enclose the reference chamber 305 preferably has uniform height, i.e., forms a solid seal rather than a circumferential seal around the reference chamber 305 as is preferably used for the test chambers 302. The reason being that such a circumferential seal may trap a minute air volume when moving the slider 300 relative to the cassette halves 200A, 200B and where this air volume will then flank the gelled sample (3D culture matrix) in the reference chamber 305. The trapped air may then dry the gelled sampled in the reference chamber 305 and cause a deformation of the gelled sample during such a drying process. However, the preferred solid seal 256 prevent or at least significantly reduces the risk of entrapment of air next to the gelled samples and thereby avoids or at least suppresses any undesired drying of the gelled sample in the reference chamber 305.

Application of a constant under pressure starts a constant flow, such as about 0.5-1.5 μl/minute, through the liquid interfaces in connection with the test chambers 302. This liquid flow goes from the reservoirs 240 and into the waste tanks 230, i.e., basically opposite to the flow direction shown in FIG. 18 during filling of the reservoirs 240. As a consequence, one side of the 3D culture matrix 500 in the test chamber 302 is exposed to the liquid 502 comprising a test agent, such as an antibiotic, whereas the other side of the 3D culture matrix 500 is exposed to the liquid 501 lacking the test agent. Hence, there is a constant concentration of the test agent in the liquid 502 flowing past one side the 3D culture matrix 500 and preferably a zero concentration of the test agent in the liquid 501 flowing past the opposite side of the 3D culture matrix. As a consequence, a linear concentration gradient of the test agent will be established and maintained over the 3D culture matrix 500.

The linear concentration gradient of the test agent is preferably formed due to diffusion of the test agent through the 3D culture matrix. Hence, the diffusion is from a so-called source side, which has a higher concentration of the test agent in the liquid relative the other side, denoted sink side. In a preferred embodiment, the flow rates of the liquids on either side of the 3D culture matrix are preferably kept substantially similar since then no flow of the liquid is present through the 3D culture matrix 500 in the test chamber 302. Substantially similar indicates that the two flow rates are preferably identical but can differ slightly due to inherent variations in the flow rate of the pumping systems. Thus, the difference in flow rate is preferably less than 10%, more preferably less than 5%, such as less than 2.5% and most preferably less than 1%.

It is also possible, in at least some of the test chambers 302, to use a combination of multiple, such as two, test agents. In such a case, concentration gradients may be established over the 3D culture matrix 500 in the test chamber 302 for all or both test agents. Alternatively, a concentration gradient is established over the 3D culture matrix 500 for one of the test agents, whereas the other test agent should be present in a substantially uniform concentration over the 3D culture matrix 500. This is possible by including the first test agent only in one of reservoirs 240 connected to a test chamber 302 whereas the second test agent is present, preferably at a same amount and concentration, in both reservoirs 240 connected to the test chamber 302. Non-limiting, but illustrative, examples of such combinations of test agents include piperacillin/tazobactam, ceftazidime/avibactam and ceftolozane/tazobactam.

As is shown in the figures, the cassette assembly 1 preferably comprises multiple test chambers 302. This means that different test agents can be provided in the different reservoirs 240 in one of the cassette halves 200A to thereby, in a single run of the cassette assembly 1, monitor and analyze the responses of microorganisms, such as bacteria, in the biological sample to the different test agents. For instance, the MIC of different antibiotics can be determined for bacteria in a biological sample to thereby select a suitable antibiotic or suitable antibiotics that can be used to combat or treat a bacterial infection in a subject.

The design of the cassette assembly 1 enables accurate formation of equal volumes of liquid in the reservoirs 240 and therefore, once the test agents provided therein in one of the cassette halves 200A, 200B become dissolved in the liquid, well-defined concentrations of test agents in the reservoirs 240 in one of the cassette halves 200A, 200B. This further means that well-defined concentration gradients of test agents can be established over the 3D culture matrices 500 in the test chambers 302 and an accurate determination of responses, such as MICs, of any microorganisms present in the sample and the 3D culture matrices 500.

In particular, the shedding or draining of liquid in the head space 235 above the waste tanks 230 by opening of the air valve 231 guarantees that each waste tank 230 in both cassette halves 200A, 200B contain the same volume of liquid that can be transferred to the respective reservoirs 240.

An aspect of the invention relates to a cassette assembly 1 comprising a cover 100, a first cassette half 200A, a second cassette half 200B and a slider 300. The cover 100 is configured to be positioned onto the first cassette half 200A and the second cassette half 200B and keep the first cassette half 200A and second cassette half 200B together with the slider 300 sandwiched between the first cassette half 200A and the second cassette half 200B. In this aspect, the slider 300 comprises N≥2 test chambers 302 in the form of through holes through the slider 300. In this aspect, each of the first cassette half 200A and the second cassette half 200B comprises N waste tanks 230 connected in series and separated by respective walls 233, and an excessive liquid tank 232 in fluid connection with the waste tanks 230 by a vertical outlet channel 234 and by an air valve 231. In this aspect, an inlet port 210 of the first cassette half 200A is configured to receive a liquid to sequentially fill each waste tank 230 and a head space 235 defined above the waste tanks 230. According to this aspect, the air valves 231 are configured to be opened to drain liquid in the head spaces 235 into the excessive liquid tanks 232 through the vertical outlet channels 234 and to form a separation of equal volumes of liquid in the waste tanks 230.

In an embodiment, the air valves 231 are configured to present a higher flow resistance to the liquid as compared to the vertical outlet channels 234 to prevent liquid from entering the excessive liquid tanks 232 through the air valves 231 during filling of the waste tanks 230.

In an embodiment, each of the first cassette half 200A and the second cassette half 200B comprises a connection port 212 configured to be aligned with respective openings 112, 113 in the cover 100. In this embodiment, the air valves 231 are configured to be opened by a first overpressure pulse applied through the openings 112, 113 in the cover 100.

In another embodiment, the air valves 231 are configured to be opened by a suction of air from the excessive liquid tanks 232 through the air valves 231 and into the head spaces 235. In this embodiment, the suction of air is caused by gravitational forces acting on liquid in the vertical outlet channels 234 or by absorption of liquid in the vertical outlet channels 234 by absorbent material comprised in the excessive liquid tanks 232.

In an embodiment, the air valves 231 are in the form of channels interconnecting the head spaces 235 and the excessive liquid tanks 232. In this embodiment, the cross-sectional dimensions of the vertical outlet channels 234 relative to the channels of the air valves 231 are configured to create an under pressure by gravitation and capillary force that is sufficiently large to draw excess liquid into the excessive liquid tank 232 but not sufficiently large to open the air valves 231 during filling of the waste tanks 230.

In an embodiment, each of the first cassette half 200A and the second cassette half 200B comprises N reservoirs 240. In this embodiment, each reservoir 240 in one of the first cassette half 200A and the second cassette half 200B comprises a respective test agent and each corresponding reservoir 240 in the other of the first cassette half 200A and the second cassette half 200B lacks the respective test agent. Furthermore, each waste tank 230 is in fluid connection with a respective reservoir 240 through a liquid channel 242 extending from the waste tank 230 turning at the slider 300 and continuing to the reservoir 240.

Corresponding reservoir 240 in the other of the first and second cassette halves 200A, 200B as used herein relates to a reservoir 240 that is in fluid connection with a same test chamber 302 in the slider 300 as a reservoir 240 in one of the first and second cassette halves 200A, 200B. This means that liquid present in the reservoir 240 comprising a particular test agent is transported through the liquid channel 242 and the upper opening 252 in the front wall 204 of the cassette half 200A, 200B to present the liquid flow with the particular test agent to one side of the 3D culture matrix 500 in the test chamber 302. Correspondingly, liquid present in the corresponding reservoir 240 lacking the particular test agent is transported through the liquid channel 242 and the upper opening 252 in the front wall 204 of the other cassette half 200A, 200B to present the liquid flow lacking the particular test agent to the other side of the 3D culture matrix 500 in the test chamber 302.

In an embodiment, each of the first cassette half 200A and the second cassette half 200B comprises a connection port 212 configured to be aligned with respective openings 112, 113 in the cover 100. In this embodiment, the equal volumes of liquid in the waste tanks 230 are configured to be pressed out from the waste tanks 230 and into the reservoirs 240 via the liquid channels 242 by application of a second over pressure pulse through the openings 112, 113 in the cover 100.

In an embodiment, each liquid channel 242 comprises a restrictive filter or slit 241. In this embodiment, the second over pressure pulse is configured to open the restrictive filters or slits 241 to allow emptying of the equal volumes of liquid in the waste tanks 230 into the reservoirs 240.

In an embodiment, the restrictive filters or slits 241 are configured to prevent liquid from passing the restrictive filters or slits 241 during filling of the waste tanks 230 but enable liquid to flow through the liquid channels 242 past the restrictive filters or slits 241 once an opening pressure of the restrictive filters or slits 241 has been overcome by application of the second over pressure pulse through the openings 112, 113 in the cover 100.

In an embodiment, each of the first cassette half 200A and the second cassette half 200B comprises a connection port 212 configured to be aligned with respective openings 112, 113 in the cover 100. In this embodiment, membranes 225 are arranged on top of the reservoirs 240 and configured to allow air but not liquid to pass through the membranes 225. Furthermore, the membranes 225 are configured to be opened by application of an under pressure pulse at the openings 112, 113 in the cover 100 to introduce a volume of air 245 between the liquid in the reservoirs 240 and the membranes 225.

In an embodiment, the slider 300 is movable relative to the first cassette half 200A and the second cassette half 200B between a sample filling position and a flow position. In this embodiment, the liquid channels 242 are in fluid connection with the test chambers 302 in the slider 300 in the flow position but not in the sample filling position.

In an embodiment, each of the first cassette half 200A and the second cassette half 200B comprises a connection port 212 configured to be aligned with respective openings 112, 113 in the cover 100. In this embodiment, liquid in the reservoirs 240 are configured to flow through the liquid channels 242 into the waste tanks 230 by application of an under pressure at the openings 112, 113 in the cover 100 when the slider 300 is in the flow position. Furthermore, one side of a respective three dimensional (3D) culture matrix 500 in the test chambers 302 is exposed to liquid 502 comprising a test agent and the other side of the respective 3D culture matrix 500 is exposed to liquid 501 lacking the test agent to establish a linear concentration gradient of the test agent over the respective 3D culture matrix 500.

In an embodiment, the slider 300 comprises a first through hole 301 in connection with a first end of the slider 300 and a second through hole 301 in connection with a second end of the slider 300. In this embodiment, each of the first cassette half 200A and the second cassette half 200B comprises a circumferential channel 215 having a first opening 254 configured to be aligned with the first through hole 301 and a second opening 254 configured to be aligned with the second through hole 301. Each of the first cassette half 200A and the second cassette half 200B also comprises a serpentine channel 216 interconnecting the circumferential channel 215 and the waste tanks 230. The inlet port 210 of the first cassette half 200A is in fluid connection with the circumferential channel 215, and the serpentine channels 216 are configured to present a higher flow resistance to the liquid as compared to the circumferential channels 215 to enable filling of the circumferential channels 215 prior to entering of the liquid into the waste tanks 230 through the serpentine channels 216.

In an embodiment, each of the first cassette half 200A and the second cassette half 200B comprises a vertical inlet channel 236 in fluid connection at its lower end with the serpentine channel 216 and in fluid connection with the waste tanks 230 in its upper end.

In an embodiment, the slider 300 is movable relative to the first cassette half 200A and the second cassette half 200B between a sample filling position and a flow position. In this embodiment, one of the first cassette half 200A and the second cassette half 200B comprises an inlet port 211 configured to receive a biological sample comprising a gel suspension that can be polymerized into three dimensional (3D) culture matrices 500 in the test chambers 302 in the slider 300 when the slider 300 is in the sample filling position. Furthermore, each of the first cassette half 200A and the second cassette half 200B comprises a channel system 260 forming, together with the test chambers 302 in the slider 300, a meander pattern and configured to sequentially fill the test chambers 302 with the biological sample received at the inlet port 211.

In an embodiment, the slider 300 is configured to be moved relative to the first cassette half 200A and the second cassette half 200B from the sample filling position into the flow position once the gel suspension has been polymerized into the 3D culture matrices 500 in the test chambers 302. In this embodiment, the relative movement between the slider 300 and the first cassette half 200A and the second cassette half 200B is configured to cut the polymerized biological sample to form well defined sides of the 3D culture matrices 500 and to align the sides of the 3D culture matrices 500 with liquid openings 252 in front walls 204 of the first cassette half 200A and the second cassette half 200B.

In an embodiment, each of the first cassette half 200A and the second cassette half 200B comprises a front wall 204 configured to face the slider 300. In this embodiment, the front walls comprises N pairs of openings 252, 253 comprising a respective upper opening 252 in fluid connection with a respective liquid channel 242 and a respective lower opening 253 forming part of the channel system 260. Furthermore, optional but preferred gaskets or seals 251 are arranged in the front walls 204 to circumferentially enclose the openings 252, 253.

In an embodiment, the cover 100 comprises a lid 105 and supporting structures extending from the lid 105 and supporting a slider cover 122 comprising windows 123 configured to be aligned with the test chambers 302 in the slider 300 to provide visual access through the slider cover 122 into the test chambers 302.

Another aspect of the invention relates to a cassette assembly 1 comprising a cover 100, a first cassette half 200A, a second cassette half 200B and a slider 300. The cover 100 is configured to be positioned onto the first cassette half 200A and the second cassette half 200B and keep the first cassette half 200A and second cassette half 200B together with the slider 300 sandwiched between the first cassette half 200A and the second cassette half 200B. In this aspect, the slider 300 comprises a first through hole 301 in connection with a first end of the slider 300 and a second through hole 301 in connection with a second end of the slider 300. In this aspect, each of the first cassette half 200A and the second cassette half 200B comprises a circumferential channel 215 having a first opening 254 configured to be aligned with the first through hole 301 and a second opening 254 configured to be aligned with the second through hole 301. Each of the first cassette half 200A and the second cassette half 200B further comprises N≥2 waste tanks 230 connected in series and separated by respective walls 233. Each of the first cassette half 200A and the second cassette half 200B also comprises a serpentine channel 216 interconnecting the circumferential channel 215 and the waste tanks 230. The first cassette half 200A comprises, in this aspect, an inlet port 210 in fluid connection with the circumferential channel 215. According to this aspect, the serpentine channels 216 are configured to present a higher flow resistance to the liquid as compared to the circumferential channels 215 to enable filling of the circumferential channels 215 prior to entering of the liquid into the waste tanks 230 through the serpentine channels 216.

In an embodiment, each of the first cassette half 200A and the second cassette half 200B comprises a vertical inlet channel 236 in fluid connection at its lower end with the serpentine channel 216 and in fluid connection with the waste tanks 230 in its upper end.

A further aspect of the invention relates to a cassette assembly 1 comprising a cover 100, a first cassette half 200A, a second cassette half 200B and a slider 300. The cover 100 is configured to be positioned onto the first cassette half 200A and the second cassette half 200B and keep the first cassette half 200A and second cassette half 200B together with the slider 300 sandwiched between the first cassette half 200A and the second cassette half 200B. In this aspect, the slider 300 comprises N≥2 test chambers 302 in the form of through holes through the slider 300. In this aspect, the slider 300 is movable relative to the first cassette half 200A and the second cassette half 200B between a sample filling position and a flow position. One of the first cassette half 200A and the second cassette half 200B comprises an inlet port 211 configured to receive a biological sample comprising a gel suspension that can be polymerized into three dimensional (3D) culture matrices 500 in the test chambers 302 in the slider 300 when the slider 300 is in the sample filling position. According to this aspect, each of the first cassette half 200A and the second cassette half 200B comprises a channel system 260 forming, together with the test chambers 302 in the slider 300, a meander pattern and configured to sequentially fill the test chambers 302 with the biological sample received at the inlet pot 211.

In an embodiment, the slider 300 is configured to be moved relative to the first cassette half 200A and the second cassette half 200B from the sample filling position into the flow position once the gel suspension has been polymerized into the 3D culture matrices 500 in the test chambers 302. In this embodiment, the relative movement between the slider 300 and the first cassette half 200A and the second cassette half 200B is configured to cut the polymerized biological sample to form well defined sides of the 3D culture matrices 500 and to align the sides of the 3D culture matrices 500 with liquid openings 252 in front walls 204 of the first cassette half 200A and the second cassette half 200B.

In an embodiment, each of the first cassette half 200A and the second cassette half 200B comprises a front wall 204 configured to face the slider 300. In this embodiment, the front walls comprises N pairs of openings 252, 253 comprising a respective upper opening 252 in fluid connection with a respective liquid channel 242 and a respective lower opening 253 forming part of the channel system 260. Optional gaskets or seals 251 are arranged in the front walls 204 to circumferentially enclose the openings 252, 253.

The cassette assembly 1 can be made by polymer materials, such as plastics, using, for instance, injection molding. In more detail, the cover 100 can be made of any polymer or plastic material having sufficient stiffness to keep the main components of the cassette assembly 1 together. An illustrative, but non-limiting, example of a suitable material for the cover 100 is polycarbonate (PC). The two cassette halves 200A, 200B can be made of any polymer or plastic material that is inert to the test agents preloaded into the reservoirs 240. This means that the material of the cassette halves 200A, 200B should not react with or decompose the test agents. In an embodiment, the polymer or plastic material of the cassette halves 200A, 200B is a hydrophobic polymer or plastic material. In such a case, the hydrophobicity of the material can be used to produce a (back) pressure in the meander channels. In addition, or alternatively, the polymer or plastic material is preferably optically transparent to enable monitoring the liquid level in the reservoirs 240 through the windows 121 in the cover 100. An illustrative, but non-limiting, example of a suitable material for the cassette halves 200A, 200B is polypropylene (PP). The slider 300 can be made of any polymer or plastic material that is inert to the sample loaded into the test chambers 302. The material preferably also presents sufficient adhesion to the 3D culture matrices 500 in the test chambers 302 to prevent the 3D culture matrices 500 from being pushed out of the test chambers 302 and into the fluidic system of the cassette halves 200A, 200B. The slider 300 is preferably also made of an optically transparent material to enable monitoring of the 3D culture matrices 500 in the test chambers 302 with a suitable optical, preferably microscopy-based system. Illustrative, but non-limiting, examples of suitable materials for the slider 300 include polyester, such as Eastar™ copolyester MN211; styrene methyl methacrylate (SMMA), such as NAS® 30; styrene-butadiene copolymer (SBC), such as Styrolux® T.

The response of microorganisms, such as bacteria, to the established concentration gradients of test agents, such as antibiotics, can be determined by monitoring the 3D culture matrices 500 present in the test chambers 302 either from above, i.e., through the windows 123 in the slider cover 122 of the cover 100 that are aligned with the test chambers 302, or from below. In either case, light is preferably provided from the other side of the slider 300, i.e., from above if the monitoring is done from below and from below if the monitoring is done from above of the slider 300.

The monitoring or analysis of the responses of microorganisms to the test agents can be performed as disclosed in WO 2015/005863. Briefly, a response of the microorganisms to the test agent can be determined based on a position, relative to one of the sides of the 3D culture matrix 500, of any border zone in the 3D culture matrix between a first response zone, in which the microorganism shows a first response to the test agent, and a second response zone, in which the microorganism shows a second, different response to the test agent.

In a particular embodiment, the response of the microorganism to the test agent can be determined based on the position, relative to one of the sides of the 3D culture matrix 500, of the any border zone in the 3D culture matrix and based on a width of the border zone. In another particular embodiment, the response of the microorganism to the test agent is determined based on the position, relative to one of the sides of the 3D culture matrix 500, of the any border zone in the 3D culture matrix 500 and based on a shape of the border zone and optionally based on the width of the border zone For instance, if the test agent is an antibiotic or another bactericide or bacteriostat the second response zone, in which the microorganisms, here represented by bacteria, are exposed to a comparatively low concentration of the test agent, could be the portion of the 3D culture matrix 500 with viable and growing bacteria. The first response zone is then preferably the portion of the 3D culture matrix 500 where there is substantially no viable or growing bacteria, hence the first response zone is characterized by a relative lack of bacteria (due to cell death or no cell growth). The border zone then constitutes the border or portion between the growing/viable portion and the non-growing/cell death portion.

The position of the border zone thereby provides information of the particular concentration of the test agent at which the response of the microorganisms to the test agents changes from the response occurring in the first response zone to the response occurring in the second response zone. A particular example of such a concentration of a test agent that can be determined based on the position of the border zone is MIC.

The width of the border zone provides additional information of the microorganisms and their response to the test agent. For instance, if the width of the border zone is substantially zero, i.e. basically a boundary or border between the first and second response zones, the change in response of the microorganisms occurs at a specific concentration of the test agent. However, if the border zone has a substantially non-zero width the change in response of the microorganisms occurs at a concentration range corresponding to the respective ends of the border zone.

A border zone with a non-zero width may further provide information with regard to any resistance of the microorganisms to the test agent. Hence, an extended border zone may imply that a resistance to the test agent is present in some of the microorganisms, for instance since they are able to grow at concentrations of the test agent which otherwise kill or prevent growth to non-resistant microorganisms. This means that the width of the border zone can be used in order to determine or detect any resistance at a given time of the microorganisms to the test agent.

In fact, it is actually possible with the cassette assembly 1 of the embodiments to detect any mutation in the microorganisms that induced resistance to the test agent or indeed caused loss of resistance to the test agent. Thus, the width of the border zone over time could be monitored when running the cassette assembly 1 with the culture of microorganisms in the 3D culture matrix 500. An increase in the width of the border zone over time then typically implies gain of resistance to the test agent among at least some of the microorganisms. Correspondingly, a decrease in the width of the border zone typically implies loss of resistance to the test agent among microorganisms that previously showed resistance to the test agent.

In an embodiment, see FIG. 25, an analysis instrument 25 of a system 600 can be used to take at least one image of the 3D culture matrix 500 and process the at least one image in order to identify the border zone in the image, including its position and optionally width and/or shape. Alternatively, the processing of the at least one image is performed by a processor 620 of or connected to the analysis instrument 610. The analysis instrument 610 may take the at least one image of the 3D culture matrix 500 using, for instance, a dark-field microscopy, a bright-field microscope or a phase-contrast microscope and then process the at least one image by a computer or processor 620 configured to identify the border zone based on detected light intensity in the at least one image.

In a particular embodiment, the analysis instrument 610 comprises a microscope and camera that are used to take images of the 3D culture matrices 500. In an embodiment, the analysis instrument 610 moves the microscope and camera step-by-step between the 3D culture matrices 500 in the slider 300. The slider 300 may then preferably comprise a respective marking or identifier in connection with each test chamber 302 to thereby clearly identify the particular 3D culture matrix 500 in an image taken by the camera at a given position relative to the cassette assembly 1. In another embodiment, the analysis instrument 610 comprises a camera configured to take an image of multiple, such as all, 3D culture matrices 500. This embodiment thereby relaxes the need for moving the camera between the 3D culture matrices 500.

Yet another aspect of the invention relates to a system 600 for determining a response of microorganisms to test agents, see FIG. 25. The system 600 comprises a cassette assembly 1 according to any of the embodiments. The system 600 also comprises an analysis instrument 610 configured to take at least one image of three dimensional (3D) culture matrices 500 in the test chamber 302. The 3D culture matrices 500 are formed by polymerization of a biological sample comprising the microorganisms and a gel suspension. The system 600 also comprises a processor 620 configured to determine a response of the microorganisms to test agents based on the at least one image of the 3D culture matrices 500.

In FIG. 25, the processor 620 has been illustrated as a separate unit connected, by wired or wirelessly, to the analysis instrument 610. For instance, the processor 620 could represent or form part of a computer connected to, and optionally controlling, the analysis instrument 610. In another embodiment, the analysis instrument 610 comprises the processor 620.

The cassette assembly 1 of the invention can be used to determine the identity of and to monitor various microorganisms, test agents and responses. Hence, the invention finds many different uses within hospital clinics, laboratories, diagnostic laboratories, healthcare facilities, etc.

For instance, the cassette assembly 1 can be used to identify MIC, or other concentration thresholds that have an effect or no effect, of a bioactive compound in order to identify the minimum concentration of the bioactive compound that has an effect on any given microorganism with regard to growth, proliferation, death or survival of the microorganism.

Furthermore, by establishing MIC for a set of different test agents, the phenotypic identity of a tested microorganism can be established in, for example, a diagnostic test. The analysis of phenotype could result in either full identification of the microorganism strain or result in a general classification of the microorganism with regard to responses to various test agents.

The cassette assembly 1 can also be used to follow the change of MIC for a test agent on the growth, proliferation, viability or other behavioural aspect of the microorganism over time. This approach enables monitoring of development or loss of resistance, such as antibiotic resistance, in the microorganism over time through several generations, thereby altering the ability of the microorganism to metabolize or resist the effects of the test agent. This type of experiment can be used to provide an indication of suitable clinical dose of the test agent and/or frequency of administration. Hence, the cassette assembly 1 can be used to study both the pharmacodynamics and the pharmacokinetics of any test agent or combination of test agents in any given type of microorganism.

The cassette assembly 1 can further be used to evaluate and identify combinations of test agents, such as antibiotics, which together are more efficient than the individual agents, or to evaluate if the test agents have synergistic effect, or if they together have no effects on, for example, the growth, proliferation, viability or other behavioural aspect of the microorganism.

The cassette assembly 1 can be used to screen novel drugs or chemical compounds for their effects on microorganism growth, proliferation, viability, death, ability to spread, or other behavioural aspects of the microorganism.

The cassette assembly 1 can also be used to quickly get a first profile of response of any given microorganism to agents used in clinical practice. The aim could then be to identify agents that are suitable for anti-microorganism treatment of patients suffering from microbial infections. This can be used even in cases where the life of the patient depends on a fast identification of the microorganism causing the infection in order to design an appropriate treatment.

The cassette assembly 1 can further be used to study the effects of drugs or test agents on host cells that have been infected with viruses, with effects on cell behaviour, cell survival, cell proliferation, cell death and/or cell differentiation used as readouts for the amount and effect of the viruses and test agents on the host cells. In this application, the viruses are preferably placed together with the cells that they are known to be able to infect. Thus, both direct effects on the virus particles as well as on the infected host cells, such as cytopathic effects, can be used to study the effects of test agents at different concentrations.

As an example of the study of the effects of drugs on parasites, Malaria parasites could be studied using human or mouse red blood cells infected with the parasite and cultured in the 3D culture matrix 500 of the cassette assembly 1. The response of the parasites and red blood cells to one or more gradients of drug(s) can then be tested.

Culturing microorganisms in a 3D culture matrix 500 in test chambers 302 of a cassette assembly 1 enables keeping the microorganisms inside the closed test chambers 302. This provides protection for the personnel against potentially harmful microorganisms but also protects against contamination of the sample in the 3D culture matrices 500.

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible.

The invention claimed is:

1. A cassette assembly comprising:
a cover;
a first cassette half;
a second cassette half; and
a slider, wherein
the cover is configured to be positioned onto the first cassette half and the second cassette half and keep the first cassette half and second cassette half together with the slider sandwiched between the first cassette half and the second cassette half;
the slider comprises N≥2 test chambers in the form of through holes through the slider;
each of the first cassette half and the second cassette half comprises:
N waste tanks connected in series and separated by respective walls; and
an excessive liquid tank in fluid connection with the waste tanks by a vertical outlet channel and by an air valve;
an inlet port of the first cassette half is configured to receive a liquid to sequentially fill each waste tank and a head space defined above the waste tanks; and
the air valves are configured to be opened to drain liquid in the head spaces into the excessive liquid tanks through the vertical outlet channels and to form a separation of equal volumes of liquid in the waste tanks;
wherein each of the first cassette half and the second cassette half comprises N reservoirs;
each reservoir in one of the first cassette half and the second cassette half comprises a respective test agent and each corresponding reservoir in the other of the first cassette half and the second cassette half lacks the respective test agent; and
each waste tank is in fluid connection with a respective reservoir through a liquid channel extending from the waste tank turning at the slider and continuing to the reservoir.

2. The cassette assembly according to claim 1, wherein the air valves are configured to present a higher flow resistance to the liquid as compared to the vertical outlet channels to prevent liquid from entering the excessive liquid tanks through the air valves during filling of the waste tanks.

3. The cassette assembly according to claim 1, wherein each of the first cassette half and the second cassette half comprises a connection port configured to be aligned with respective openings in the cover; and
the air valves are configured to be opened by a first overpressure pulse applied through the openings in the cover.

4. The cassette assembly according to claim 1, wherein the air valves are configured to be opened by a suction of air from the excessive liquid tanks through the air valves and into the head spaces; and
the suction of air is caused by gravitational forces acting on liquid in the vertical outlet channels or by absorption of liquid in the vertical outlet channels by absorbent material comprised in the excessive liquid tanks.

5. The cassette assembly according to claim 1, wherein the air valves are in the form of channels interconnecting the head spaces and the excessive liquid tanks;
the cross-sectional dimensions of the vertical outlet channels relative to the channels of the air valves are configured to create an under pressure by gravitation and capillary force that is sufficiently large to draw excess liquid into the excessive liquid tank but not sufficiently large to open the air valves during filling of the waste tanks.

6. The cassette assembly according to claim 1, wherein each of the first cassette half and the second cassette half comprises a connection port configured to be aligned with respective openings in the cover; and
the equal volumes of liquid in the waste tanks are configured to be pressed out from the waste tanks and into the reservoirs via the liquid channels by application of a second over pressure pulse through the openings in the cover.

7. The cassette assembly according to claim 6, wherein each liquid channel comprises a restrictive filter or slit; and
the second over pressure pulse is configured to open the restrictive filters or slits to allow emptying of the equal volumes of liquid in the waste tanks into the reservoirs.

8. The cassette assembly according to claim 7, wherein the restrictive filters or slits are configured to prevent liquid from passing the restrictive filters or slits during filling of the waste tanks but enable liquid to flow through the liquid channels past the restrictive filters or slits once an opening pressure of the restrictive filters or slits has been overcome by application of the second over pressure pulse through the openings in the cover.

9. The cassette assembly according to claim 1, wherein each of the first cassette half and the second cassette half comprises a connection port configured to be aligned with respective openings in the cover;
membranes are arranged on top of the reservoirs and configured to allow air but not liquid to pass through the membranes; and
the membranes are configured to be opened by application of an under pressure pulse at the openings in the cover to introduce a volume of air between the liquid in the reservoirs and the membranes.

10. The cassette assembly according to claim 1, wherein the slider is movable relative to the first cassette half and the second cassette half between a sample filling position and a flow position; and
the liquid channels are in fluid connection with the test chambers in the slider in the flow position but not in the sample filling position.

11. The cassette assembly according to claim 10, wherein each of the first cassette half and the second cassette half comprises a connection port configured to be aligned with respective openings in the cover;
liquid in the reservoirs are configured to flow through the liquid channels into the waste tanks by application of an under pressure at the openings in the cover when the slider is in the flow position; and one side of a respective three dimensional (3D) culture matrix in the test chambers is exposed to liquid comprising a test agent and the other side of the respective 3D culture matrix is exposed to liquid lacking the test agent to establish a linear concentration gradient of the test agent over the respective 3D culture matrix.

12. The cassette assembly according to claim 1, wherein the slider comprises a first through hole in connection with a first end of the slider and a second through hole in connection with a second end of the slider;

each of the first cassette half and the second cassette half comprises:

a circumferential channel having a first opening configured to be aligned with the first through hole and a second opening configured to be aligned with the second through hole;

a serpentine channel interconnecting the circumferential channel and the waste tanks;

the inlet port of the first cassette half is in fluid connection with the circumferential channel; and the serpentine channels are configured to present a higher flow resistance to the liquid as compared to the circumferential channels to enable filling of the circumferential channels prior to entering of the liquid into the waste tanks through the serpentine channels.

13. The cassette assembly according to claim 12, wherein each of the first cassette half and the second cassette half comprises a vertical inlet channel in fluid connection at its lower end with the serpentine channel and in fluid connection with the waste tanks in its upper end.

14. The cassette assembly according to claim 1, wherein the slider is movable relative to the first cassette half and the second cassette half between a sample filling position and a flow position;

one of the first cassette half and the second cassette half comprises an inlet port configured to receive a biological sample comprising a gel suspension that can be polymerized into three dimensional (3D) culture matrices in the test chambers in the slider when the slider is in the sample filling position; and each of the first cassette half and the second cassette half comprises a channel system forming, together with the test chambers in the slider, a meander pattern and configured to sequentially fill the test chambers with the biological sample received at the inlet port.

15. The cassette assembly according to claim 14 wherein the slider is configured to be moved relative to the first cassette half and the second cassette half from the sample filling position into the flow position once the gel suspension has been polymerized into the 3D culture matrices in the test chambers; and the relative movement between the slider and the first cassette half and the second cassette half is configured to cut the polymerized biological sample to form well defined sides of the 3D culture matrices and to align the sides of the 3D culture matrices with liquid openings in front walls of the first cassette half and the second cassette half.

16. The cassette assembly according to claim 14, wherein each of the first cassette half and the second cassette half comprises N reservoirs;

each reservoir in one of the first cassette half and the second cassette half comprises a respective test agent and each corresponding reservoir in the other of the first cassette half and the second cassette half lacks the respective test agent;

each waste tank is in fluid connection with a respective reservoir through a liquid channel extending from the waste tank turning at the slider and continuing to the reservoir;

each of the first cassette half and the second cassette half comprises a front wall configured to face the slider; and each front wall comprises N pairs of openings comprising a respective upper opening in fluid connection with a respective liquid channel and a respective lower opening forming part of the channel system.

17. The cassette assembly according to claim 16, further comprising gaskets or seals arranged in the front walls to circumferentially enclose the openings.

18. The cassette assembly according to claim 1, wherein the cover comprises a lid and supporting structures extending from the lid and supporting a slider cover comprising windows configured to be aligned with the test chambers in the slider to provide visual access through the slider cover into the test chambers.

19. A system for determining a response of microorganisms to test agents comprising:

a cassette assembly according to claim 1;

an analysis instrument configured to take at least one image of three dimensional (3D) culture matrices in the test chamber, wherein the 3D culture matrices are formed by polymerization of a biological sample comprising the microorganisms and a gel suspension; and a processor configured to determine a response of the microorganisms to test agents based on the at least one image of the 3D culture matrices.

20. A cassette assembly comprising:

a cover;

a first cassette half;

a second cassette half; and a slider, wherein the cover is configured to be positioned onto the first cassette half and the second cassette half and keep the first cassette half and second cassette half together with the slider sandwiched between the first cassette half and the second cassette half;

the slider comprises N≥2 test chambers in the form of through holes through the slider;

each of the first cassette half and the second cassette half comprises:

N waste tanks connected in series and separated by respective walls; and an excessive liquid tank in fluid connection with the waste tanks by a vertical outlet channel and by an air valve;

an inlet port of the first cassette half is configured to receive a liquid to sequentially fill each waste tank and a head space defined above the waste tanks; and the air valves are configured to be opened to drain liquid in the head spaces into the excessive liquid tanks through the vertical outlet channels and to form a separation of equal volumes of liquid in the waste tanks;

wherein the slider comprises a first through hole in connection with a first end of the slider and a second through hole in connection with a second end of the slider;

each of the first cassette half and the second cassette half comprises:

a circumferential channel having a first opening configured to be aligned with the first through hole and a second opening configured to be aligned with the second through hole;

a serpentine channel interconnecting the circumferential channel and the waste tanks;

the inlet port of the first cassette half is in fluid connection with the circumferential channel; and the serpentine channels are configured to present a higher flow resistance to the liquid as compared to the circumferential channels to enable filling of the circumferential channels prior to entering of the liquid into the waste tanks through the serpentine channels.

21. The cassette assembly according to claim 20, wherein each of the first cassette half and the second cassette half comprises a vertical inlet channel in fluid connection at its lower end with the serpentine channel and in fluid connection with the waste tanks in its upper end.

22. A cassette assembly comprising:

a cover;

a first cassette half;

a second cassette half; and a slider, wherein the cover is configured to be positioned onto the first cassette half and the second cassette half and keep the first cassette half and second cassette half together with the slider sandwiched between the first cassette half and the second cassette half;

the slider comprises N≥2 test chambers in the form of through holes through the slider;

each of the first cassette half and the second cassette half comprises:

N waste tanks connected in series and separated by respective walls; and an excessive liquid tank in fluid connection with the waste tanks by a vertical outlet channel and by an air valve;

an inlet port of the first cassette half is configured to receive a liquid to sequentially fill each waste tank and a head space defined above the waste tanks; and the air valves are configured to be opened to drain liquid in the head spaces into the excessive liquid tanks through the vertical outlet channels and to form a separation of equal volumes of liquid in the waste tanks;

wherein the slider is movable relative to the first cassette half and the second cassette half between a sample filling position and a flow position;

one of the first cassette half and the second cassette half comprises an inlet port configured to receive a biological sample comprising a gel suspension that can be polymerized into three dimensional (3D) culture matrices in the test chambers in the slider when the slider is in the sample filling position; and each of the first cassette half and the second cassette half comprises a channel system forming, together with the test chambers in the slider, a meander pattern and configured to sequentially fill the test chambers with the biological sample received at the inlet port.

23. The cassette assembly according to claim 22 wherein the slider is configured to be moved relative to the first cassette half and the second cassette half from the sample filling position into the flow position once the gel suspension has been polymerized into the 3D culture matrices in the test chambers; and the relative movement between the slider and the first cassette half and the second cassette half is configured to cut the polymerized biological sample to form well defined sides of the 3D culture matrices and to align the sides of the 3D culture matrices with liquid openings in front walls of the first cassette half and the second cassette half.

24. The cassette assembly according to claim 22, wherein each of the first cassette half and the second cassette half comprises N reservoirs;

each reservoir in one of the first cassette half and the second cassette half comprises a respective test agent and each corresponding reservoir in the other of the first cassette half and the second cassette half lacks the respective test agent;

each waste tank is in fluid connection with a respective reservoir through a liquid channel extending from the waste tank turning at the slider and continuing to the reservoir;

each of the first cassette half and the second cassette half comprises a front wall configured to face the slider; and each front wall comprises N pairs of openings comprising a respective upper opening in fluid connection with a respective liquid channel and a respective lower opening forming part of the channel system.

25. The cassette assembly according to claim 24, further comprising gaskets or seals arranged in the front walls to circumferentially enclose the openings.

* * * * *